(12) United States Patent
He et al.

(10) Patent No.: US 9,029,169 B2
(45) Date of Patent: May 12, 2015

(54) PROTEIN RENATURATION MICROFLUIDIC DEVICES AND METHODS OF MAKING AND USING THE SAME

(75) Inventors: Mei He, Albany, CA (US); Amy E. Herr, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 595 days.

(21) Appl. No.: 13/309,343

(22) Filed: Dec. 1, 2011

(65) Prior Publication Data

US 2012/0142904 A1    Jun. 7, 2012

Related U.S. Application Data

(60) Provisional application No. 61/419,761, filed on Dec. 3, 2010, provisional application No. 61/560,167, filed on Nov. 15, 2011.

(51) Int. Cl.
*B01D 57/02* (2006.01)
*C07K 1/113* (2006.01)
*C07K 1/26* (2006.01)
(Continued)

(52) U.S. Cl.
CPC .............. *B01D 57/02* (2013.01); *C07K 1/1136* (2013.01); *C07K 1/26* (2013.01); *C07K 1/36* (2013.01); *G01N 27/453* (2013.01); *G01N 33/483* (2013.01); *G01N 33/5302* (2013.01); *G01N 33/561* (2013.01); *B01L 3/502753* (2013.01); *B01L 3/502776* (2013.01); *B01L 2200/0636* (2013.01); *B01L 2300/0816* (2013.01); *B01L 2300/0861* (2013.01); *B01L 2400/0421* (2013.01)

(58) Field of Classification Search
CPC ... B01D 57/02; G01N 21/453; G01N 33/483; B01L 3/502753; B01L 5/502776
See application file for complete search history.

(56) References Cited

U.S. PATENT DOCUMENTS 5,407,546 A    4/1995  Schickle
5,420,016 A    5/1995  Boguslaski et al.
(Continued)

FOREIGN PATENT DOCUMENTS

JP    2004-61319 A    2/2004
JP    2006-10529 A    1/2006
(Continued)

OTHER PUBLICATIONS

Office Action dated Jul. 8, 2014 issued in corresponding Japanese Patent Application No. 2012-511973.
(Continued)

*Primary Examiner* — Melanie Y Brown
(74) *Attorney, Agent, or Firm* — Rudy J. Ng; Bret E. Field; Bozicevic, Field & Francis LLP

(57) ABSTRACT

Microfluidic devices having a protein renaturation component and methods for using the same are provided. Aspects of the present disclosure include microfluidic devices that include a separation medium with a first flow path and a protein renaturation component in fluid communication with the separation medium and having a second flow path. Also provided are methods of using the devices as well as systems and kits that include the devices. The devices, systems and methods find use in a variety of different applications, including diagnostic and validation assays.

23 Claims, 26 Drawing Sheets

(51) Int. Cl.
*C07K 1/36* (2006.01)
*G01N 27/453* (2006.01)
*G01N 33/483* (2006.01)
*G01N 33/53* (2006.01)
*G01N 33/561* (2006.01)
*B01L 3/00* (2006.01)

(56) References Cited

U.S. PATENT DOCUMENTS

| | | |
|---|---|---|
| 5,637,469 A | 6/1997 | Wilding et al. |
| 5,858,195 A | 1/1999 | Ramsey |
| 6,499,499 B2 | 12/2002 | Dantsker et al. |
| 6,613,581 B1 | 9/2003 | Wada et al. |
| 6,818,112 B2 | 11/2004 | Schneider et al. |
| 6,969,452 B2 | 11/2005 | He et al. |
| 6,974,526 B2 | 12/2005 | Lee et al. |
| 7,112,444 B2 | 9/2006 | Beebe et al. |
| 7,235,389 B2 | 6/2007 | Lim et al. |
| 7,241,421 B2 | 7/2007 | Webster et al. |
| 7,641,780 B2 | 1/2010 | Lee et al. |
| 7,754,150 B2 | 7/2010 | Wada et al. |
| 8,329,016 B1 | 12/2012 | Sommer et al. |
| 2001/0041332 A1 | 11/2001 | Hillebrand et al. |
| 2002/0153046 A1 | 10/2002 | Dantsker et al. |
| 2003/0089605 A1 | 5/2003 | Timperman |
| 2003/0127331 A1 | 7/2003 | Leka |
| 2004/0112751 A1* | 6/2004 | Han et al. ............. 204/605 |
| 2004/0158890 A1 | 8/2004 | Thomashow et al. |
| 2004/0209354 A1 | 10/2004 | Mathies et al. |
| 2005/0020814 A1 | 1/2005 | Rudolph et al. |
| 2005/0106740 A1 | 5/2005 | Boyes et al. |
| 2005/0155861 A1 | 7/2005 | Guzman et al. |
| 2005/0217996 A1 | 10/2005 | Liu et al. |
| 2005/0269267 A1 | 12/2005 | Patton et al. |
| 2006/0191792 A1 | 8/2006 | Herr et al. |
| 2006/0211055 A1 | 9/2006 | Hafeman et al. |
| 2007/0121111 A1 | 5/2007 | Blumenfeld et al. |
| 2007/0131552 A1 | 6/2007 | Jung et al. |
| 2009/0071828 A1* | 3/2009 | Squires et al. ............. 204/453 |
| 2009/0194483 A1 | 8/2009 | Robotti et al. |
| 2010/0108519 A1 | 5/2010 | Soper et al. |
| 2011/0177618 A1 | 7/2011 | Herr et al. |

FOREIGN PATENT DOCUMENTS

| | | |
|---|---|---|
| JP | 2007-518977 A | 7/2007 |
| JP | 2008-537119 A | 9/2008 |
| WO | WO 00/73799 A1 | 12/2000 |
| WO | WO 02/086332 A1 | 10/2002 |
| WO | WO 2006/102516 A2 | 9/2006 |
| WO | 2010135364 | 11/2010 |
| WO | 2011106693 A2 | 9/2011 |
| WO | 2011142781 | 11/2011 |
| WO | 2012071472 A2 | 5/2012 |
| WO | 2012075308 A2 | 6/2012 |

OTHER PUBLICATIONS

Fonslow et al. 'Free-Flow Electrophoresis on an Anodically Bonded Glass Microchip' Anal. Chem., Sep. 1, 2005, vol. 77(17), pp. 5706-5710.

Song, et al. 'Electrophoretic concentration of proteins at laser-patterned nanoporous membranes in microchips.' Anal Chem., Aug. 1, 2004, vol. 76(15), pp. 4589-4592.

Zeng et al., 'Microfluidic Self-patterning of Large-Scale Crystalline Nanoarrays for High-Throughput Continuous DNA Fractionation' Angew. Chem. Int. Ed., Jul. 15, 2008, vol. 47, pp. 6388-6391.

Subramanian, "Dye-ligand affinity chromatography: the interaction of cibacron blue F3Ga with proteins and enzymes", Critical Reviews in Biochemistry and Molecular Biology, vol. 16, No. 2, pp. 169-205 (1984).

Zhang et al., "High-Speed Free-Flow Electrophoresis on Chip", Anal. Chem., vol. 75, pp. 5759-5766 (2003).

Lerch, Margaret A. et al., "Electrokinetic Fluid Control in Two-Dimensional Planar Microfluidic Devices", Anal. Chem., Aug. 25, 2007, vol. 79, No. 19, pp. 7485-7491.

Renzi et al., "Hand-Held Microanalytical Instrument for Chip-Based Electrophoretic Separations of Proteins" Anal. Chem (2005) 77, 435-441.

Song et al., "Electrophoretic Concentration of Proteins at Laser-Patterned Nanporous Membranes in Microchips" Anal. Chem (2004) 76, 4589-4592.

Zeng, Yong et al., "Microfluidic Self-patterning of Large-Scale Crystalline Nanoarrays for High-Throughput Continuous DNA Fractionation", Angew. Chem. Int. Ed., Jul. 15, 2008, vol. 47, pp. 6388-6391.

He M et al., "Microfluidic Polyacrylamide Gel Electrophoresis with in Situ Immunoblotting for Native Protein Analysis" Anal Chem (2009) 81, 8177-8184.

He et al., "Polyacrylamide Gel Photopatterning Enables Automated Protein Immunoblotting in a Two-Dimensional Microdevice" J. Am. Chem. Soc. (2010) 132, 2512-2513.

He et al., "Automated microfluidic protein immunoblotting" Nature Protocols (2010) vol. 5, No. 11; 1844-1856.

Kim et al., "Microfluidic Western Blotting: Cationic Surfactant Based Protein Sizing Integrated with Electrostatic Immobilization", IEEE MEMS 24th International Conference, pp. 197-200 (2011).

* cited by examiner

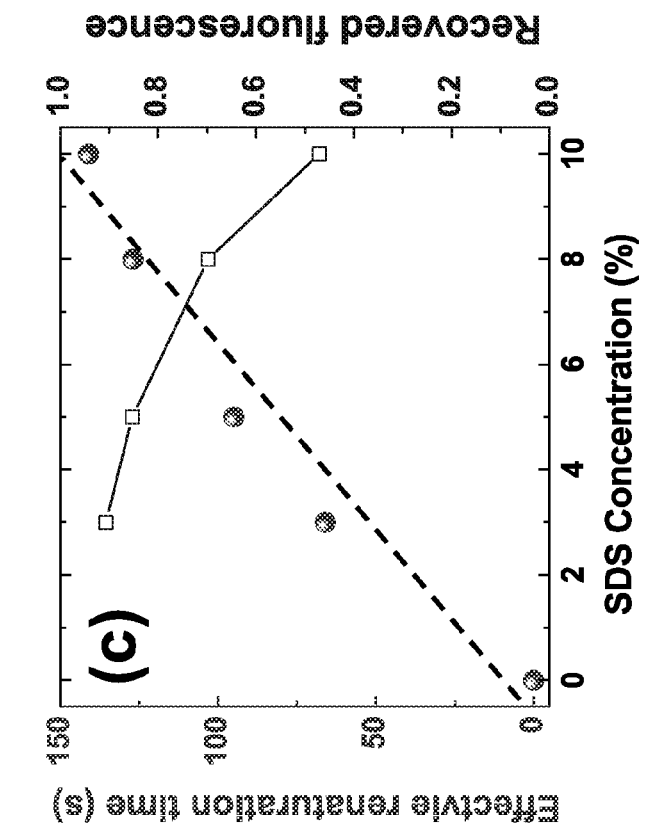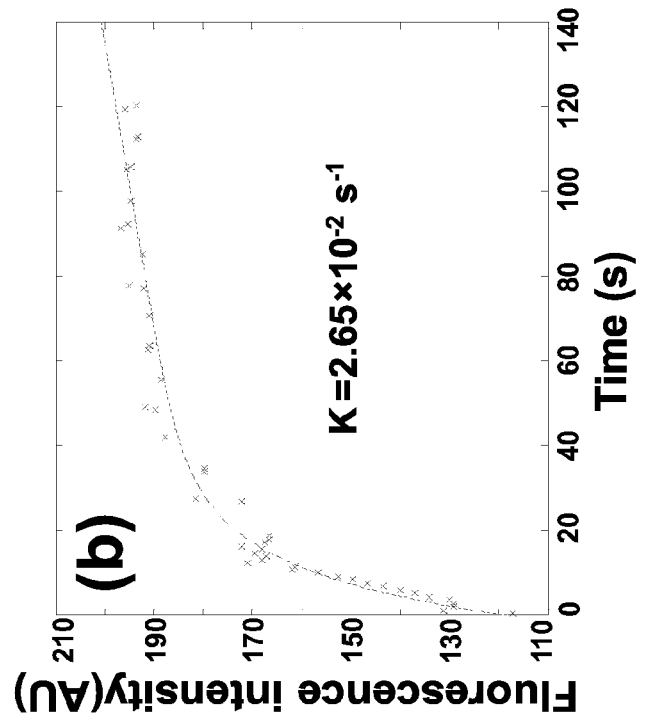
FIG. 6, continued

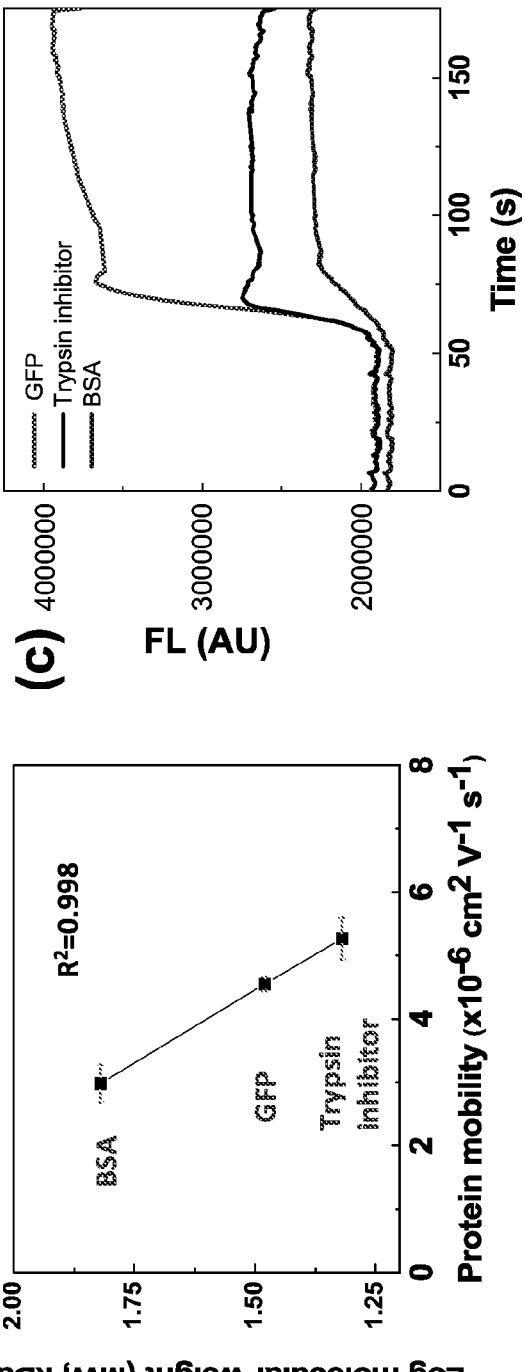
FIG. 9, continued

US 9,029,169 B2

PROTEIN RENATURATION MICROFLUIDIC DEVICES AND METHODS OF MAKING AND USING THE SAME

CROSS-REFERENCE TO RELATED APPLICATIONS

Pursuant to 35 U.S.C. §119(e), this application claims priority to U.S. Provisional Patent Application Nos. 61/419,761 filed on Dec. 3, 2010, and 61/560,167, filed on Nov. 15, 2011, the disclosures of each of which are herein incorporated by reference in their entirety.

INTRODUCTION

SDS-PAGE (sodium dodecyl sulfate polyacrylamide gel electrophoresis) is a basic tool widely used in biochemistry, cell and molecular biology, and clinical diagnosis to separate proteins on the sole basis of their size. Protein size determination is achieved through binding of SDS molecules to protein, which covers different proteins with identical negative charges per unit mass. Though several detergents have been discovered for protein PAGE sizing (e.g., cetrimonium bromide, acid-labile surfactant), SDS is still a widely used detergent for measurements of protein size in PAGE. However, SDS treatment has a significant impact on protein original structure and may decrease the normal level of biological activity. Thus, protein renaturation or removal of SDS is necessary prior to immuno-probing or mass spectrometry identification, particularly for Western blotting. Currently, several protein renaturation techniques are conducted on the benchtop, including dilution, gel filtration, and size exclusion chromatography.

SUMMARY

Microfluidic devices having a protein renaturation component and methods for using the same are provided. Aspects of the present disclosure include microfluidic devices that include a separation medium with a first flow path and a protein renaturation component in fluid communication with the separation medium and having a second flow path. Also provided are methods of using the devices as well as systems and kits that include the devices. The devices, systems and methods find use in a variety of different applications, including diagnostic and validation assays.

Aspects of the present disclosure include a microfluidic device that includes a separation medium having a first flow path and a protein renaturation component in fluid communication with the separation medium and having a second flow path.

In certain embodiments, the microfluidic device further includes a binding medium in fluid communication with the separation medium and having a third flow path. In some instances, the first flow path has a first directional axis and the second flow path has a second directional axis. In certain cases, the second flow path and the third flow path are in opposite directions along the second directional axis.

In certain embodiments, the protein renaturation component includes a sub-nanopore gel membrane. The sub-nanopore gel membrane may be polymerized from a precursor having a monomer concentration ranging from 40 to 50% T.

In some embodiments, the binding medium includes a binding member stably associated with a support. In some cases, the binding member is a proteinaceous binding member. In certain instances, the proteinaceous binding member includes an antibody or a fragment thereof. In some cases, the proteinaceous binding member includes a lectin.

In some instances, the microfluidic device includes a loading medium in fluid communication with the separation medium. In certain embodiments, the device is configured so that the renaturation component bounds a first side of the separation medium, a binding medium bounds a second side of the separation medium that is opposite the first side, and the loading medium bounds a third side of the separation medium that is between the first and second sides.

In some instances, the microfluidic device also includes a first set of side channels having the renaturation component, and a second set of side channels having the binding medium.

In certain cases, the device is configured to apply first and second electric fields of differing directions to the separation medium. In some embodiments, the first and second electric fields are orthogonal to each other.

In certain embodiments, the microfluidic device further includes a buffer. In some instances, the buffer includes a detergent. In some cases, the microfluidic device further includes a sample. In some embodiments, the sample includes an analyte of interest. In certain instances, the analyte includes a fluorescent label.

Aspects of the present disclosure include a method that includes introducing a fluid sample into a microfluidic device as described herein, directing the sample through the separation medium to produce a separated sample, and subjecting the separated sample to renaturing conditions to produce a renatured sample.

In some instances, the method also includes transferring the renatured sample to a binding medium. In some embodiments, the method further includes detecting the presence or absence of one or more analytes in the sample. In certain instances, the analyte includes a biomarker for a disease. In certain cases, the transferring includes contacting the sample to a proteinaceous binding member bound to the binding medium. In some instances, the proteinaceous binding member includes an antibody or a fragment thereof. In some cases, the proteinaceous binding member includes a lectin.

Aspects of the present disclosure include a system that includes a microfluidic device as described herein, and an electric field applicator configured to apply an electric field to a microfluidic channel of the microfluidic device. As indicated above, the microfluidic device includes a separation medium having a first flow path and a protein renaturation component in fluid communication with the separation medium and having a second flow path.

In certain embodiments, the system includes a detector configured to evaluate a microchannel of the device to obtain a signal. In some cases, the system includes microfluidic components configured to direct a fluid through the microfluidic device.

Aspects of the present disclosure also include a kit that includes a microfluidic device as described herein and a labeled binding member.

In certain embodiments, the kit includes one or more reagents, such as, but not limited to, a buffer, a detection reagent, a release reagent, a detergent, a refolding reagent and a denaturing reagent.

BRIEF DESCRIPTION OF THE FIGURES

FIG. 1(*b*) shows a schematic of a microfluidic device, including the loading medium, separation medium, protein renaturation component, and binding medium, according to embodiments of the present disclosure.

FIG. 5(a) shows a bright-field image of a microfluidic device patterned with a renaturation membrane (left) and binding medium (right). FIG. 5(b) shows a fluorescence image of the continuous loading of a stream of 5% SDS treated GFP protein. FIG. 5(c) shows a fluorescence image of the renaturation of 5% SDS treated GFP on the renaturation component. FIG. 5(d) shows a fluorescence image of the elution of GFP from the renaturation component interface after renaturation. FIG. 5(e) shows a fluorescence image of the transfer of renatured GFP to the binding medium. FIG. 5(f) shows a fluorescence image of GFP captured in the binding medium. FIG. 5(g) shows a graph of the renaturation kinetic profile of GFP observed on the renaturation component interface. FIG. 5(h) shows a graph of the GFP blotting profile after renaturation. FIG. 5(i) shows a graph of a negative control: 5% SDS treated BSA showed a significantly different renaturation profile, as BSA fluorescence was unrelated to its native state. Binding of BSA was not observed in the binding medium, as shown in the inset figure.

FIG. 8(a) shows a fluorescence image of native protein ladder separation using a microfluidic device according to embodiments of the present disclosure. FIG. 8(b) shows a fluorescence image of SDS-PAGE ladder separation using a microfluidic device according to embodiments of the present disclosure. FIG. 8(c) shows a graph of the protein molecular mass calibration curve, according to embodiments of the present disclosure.

FIG. 9(a) shows fluorescent image sequences of microfluidic Western blotting of GFP, including SDS-PAGE, transfer, renaturation, and blotting, according to embodiments of the present disclosure. FIG. 9(b) shows a graph of a molecular mass calibration curve obtained from SDS-PAGE sizing in a first flow path, according to embodiments of the present disclosure. FIG. 9(c) shows a graph of renaturation profiles for GFP, BSA, and trypsin inhibitor, according to embodiments of the present disclosure.

FIG. 10(A) shows a photograph of a glass microfluidic device with a microchamber at the center, according to embodiments of the present disclosure. FIG. 10(B) shows a schematic illustration of the three assay stages: SDS-PAGE, SDS dilution via microfiltration during protein renaturation, and probing of renatured proteins using biotinylated lectin immobilized to streptavidin acrylamide, according to embodiments of the present disclosure. "Mr" indicates molecular mass. FIG. 10(C) shows a micrograph of molecular mass cutoff (MrCO) microfilters used for post-separation SDS removal, according to embodiments of the present disclosure. FIG. 10(D) shows a schematic of biotinylated lectin (or antibody) housed in streptavidin acrylamide in a microchannel array flanking the right-hand side of the microchamber, according to embodiments of the present disclosure.

FIG. 11(A) shows a graph of the time evolution of the fluorescence signal during treatment and fit to a double-exponential function, according to embodiments of the present disclosure. The GFP concentration was 200 nM. FIG. 11(B) shows a graph of renaturation halftime and fluorescence recovery vs. the SDS concentration, according to embodiments of the present disclosure.

FIG. 13(A) shows fluorescence micrographs of two-color monitoring of Mr ladders and myeloma IgA1 sizing, according to embodiments of the present disclosure. FIG. 13(B) shows fluorescence micrographs of the time evolution of the HAA lectin blot of galactose-deficient IgA1 myeloma protein, according to embodiments of the present disclosure. FIG. 13(C) shows a graph of the evaluation of the recovered activity by comparison of the amounts of captured myeloma IgA1 in the blotting region under native and SDS conditions, according to embodiments of the present disclosure. FIG. 13(D) shows fluorescence micrographs of an HAA blot of 5% SDS treated myeloma IgA1 (green) and Mr ladders (68-200 kDa, red) without online renaturation, as a negative control, according to embodiments of the present disclosure.

FIG. 19(a) shows a graph of a regression curve for 3% SDS-GFP; FIG. 19(b) shows a graph of a regression curve for 5% SDS-GFP; FIG. 19(c) shows a graph of a regression curve for 8% SDS-GFP; and FIG. 19(d) shows a graph of a regression curve for 10% SDS-GFP.

FIG. 22 shows microfluidic devices with channels ~50 μM wide, with spacing between channels shown as: 100 μm, 50 μm, and 10 μm, indicated by the arrows.

DETAILED DESCRIPTION

Figure 1:
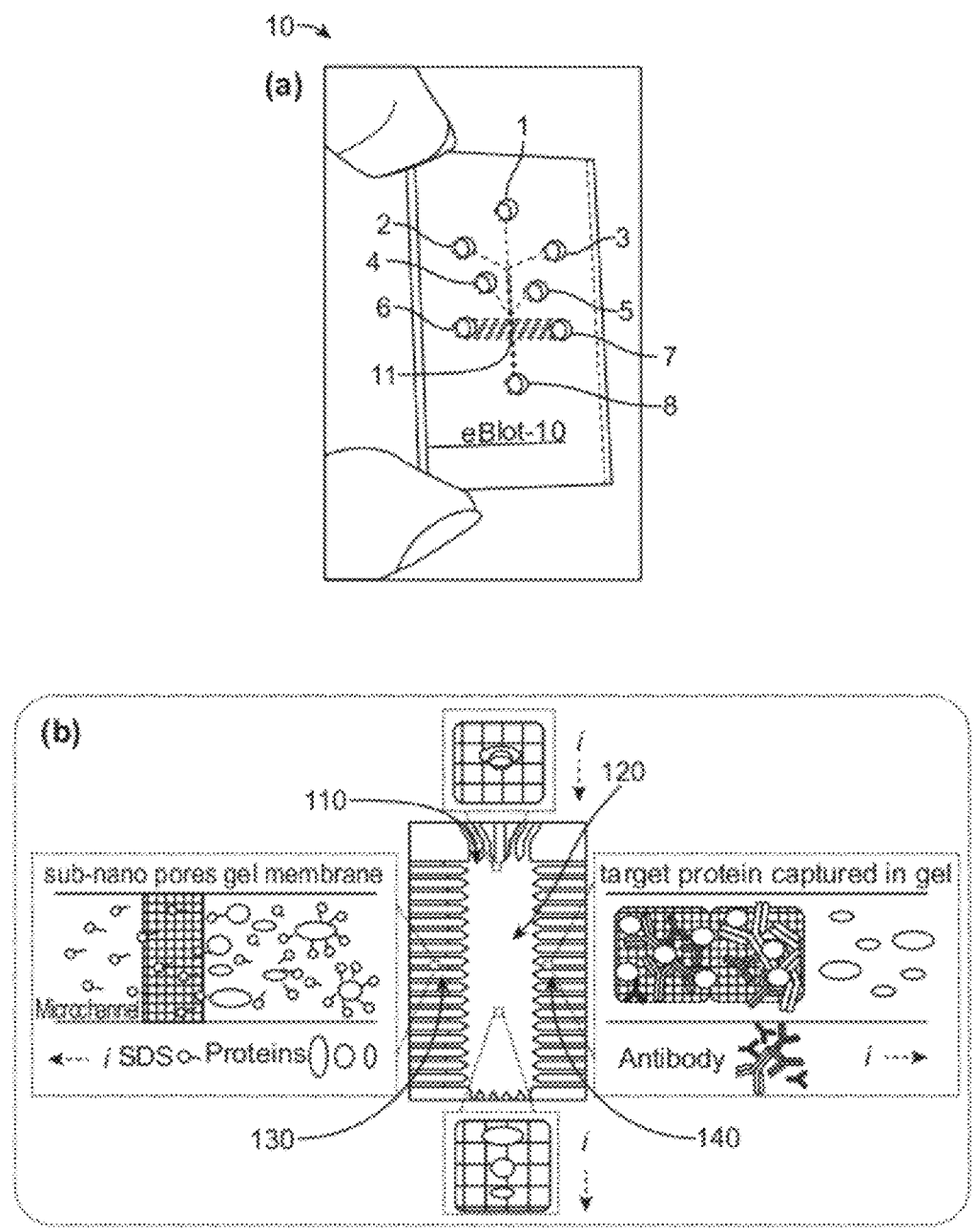
FIG. 1(*a*) shows a photograph of a microfluidic device, according to embodiments of the present disclosure.

Microfluidic devices having a protein renaturation component and methods for using the same are provided. Aspects of the present disclosure include microfluidic devices that include a separation medium with a first flow path and a protein renaturation component in fluid communication with the separation medium and having a second flow path. Also provided are methods of using the devices as well as systems and kits that include the devices. The devices, systems and methods find use in a variety of different applications, including diagnostic and validation assays.

Below, the subject microfluidic devices are described first in greater detail. Methods of detecting an analyte in a fluid sample are also disclosed in which the subject microfluidic devices find use. In addition, systems and kits that include the subject microfluidic devices are also described.

Microfluidic Devices

Aspects of the present disclosure include microfluidic devices for detecting an analyte in a fluid sample. A "microfluidic device" is device that is configured to control and manipulate fluids geometrically constrained to a small scale (e.g., sub-millimeter). Embodiments of the microfluidic devices include a separation medium and a protein renaturation component. The separation medium may be configured to separate analytes in a sample from each other. The separated analytes may be contacted with the protein renaturation component, which allows the separated sample to be subjected to protein renaturation conditions. In certain embodiments, the microfluidic device also includes a binding medium. The renatured sample may be contacted with the binding medium, which specifically binds to one or more analytes of interest in the sample. The bound analyte or analytes of interest may then be detected. Additional details about the separation medium, protein renaturation component and binding medium are discussed below.

Separation Medium

In certain embodiments, the microfluidic devices include a separation medium. The separation medium may be configured to separate analytes in a sample from each other. In some cases, the separation medium is configured to separate analytes in a sample based on the physical properties of the analytes. For example, the separation medium may be configured to separate the analytes in the sample based on the molecular mass, size, charge (e.g., charge to mass ratio), isoelectric point, etc. of the analytes. In certain instances, the separation medium is configured to separate the analytes in the sample based on the molecular mass of the analytes. In some cases, the separation medium is configured to separate the analytes in the sample based on the isoelectric point of the analytes (e.g., isoelectric point focusing). The separation medium may be configured to separate the analytes in the sample into distinct detectable bands of analytes. By "band" is meant a distinct detectable region or zone where the concentration of an analyte is significantly higher than the surrounding regions. Each band of analyte may include a single analyte or several analytes, where each analyte in a single band of analytes has substantially similar physical properties, as described above.

In certain embodiments, the separation medium is configured to separate the analytes in a sample as the sample traverses the separation medium. In some cases, the separation medium is configured to separate the analytes in the sample as the sample flows through the separation medium.

Aspects of the separation medium include that the separation medium has a flow path with a directional axis. By "flow path" is meant the direction a fluid sample travels as it moves. In some instances, the flow path is the direction the sample travels as the sample traverses a medium, such as the separation medium. The separation medium may have a flow path with a directional axis. In some embodiments, the directional axis of the separation flow path is aligned with the length of the separation medium. In these embodiments, the sample traverses the separation medium in the direction of the separation flow path of the separation medium (e.g., the sample may traverse the separation medium along the length of the separation medium). In some cases, the length of the separation medium is greater than the width of the separation medium, such as 2 times, 3 times, 4 times, 5 times, 10 times, etc. the width of the separation medium. In some instances, the separation flow path of the separation medium is defined by a region that includes the separation medium. For example, the microfluidic device may include a chamber. The chamber may include a separation region that includes the separation medium. The separation medium may be included in the chamber, such that a sample traverses the separation medium as the sample flows through the chamber. In some instances, the chamber includes the separation medium and a loading medium. The chamber may also include a protein renaturation component and a binding region that includes a binding medium. In other embodiments, the protein renaturation component and the binding medium are contained in side channels in fluid communication with the separation medium. These and further aspects of the microfluidic devices are described in greater detail in the sections below.

In certain embodiments, the separation medium includes a polymer, such as a polymeric gel. The polymeric gel may be a gel suitable for gel electrophoresis. The polymeric gel may include, but is not limited to, a polyacrylamide gel, an agarose gel, and the like. The resolution of the separation medium may depend on various factors, such as, but not limited to, pore size, total polymer content (e.g., total acrylamide content, % T), concentration of cross-linker (e.g., bisacrylamide concentration, % C), applied electric field, assay time, and the like. For instance, the resolution of the separation medium may depend on the pore size of the separation medium. In some cases, the pore size depends on the total polymer content of the separation medium and/or the concentration of cross-linker in the separation medium. In certain instances, the separation medium is configured to resolve analytes with molecular mass differences of 50,000 Da or less, or 25,000 Da or less, or 10,000 Da or less, such as 7,000 Da or less, including 5,000 Da or less, or 2,000 Da or less, or 1,000 Da or less, for example 500 Da or less, or 100 Da or less. In some cases, the separation medium may include a polyacrylamide gel that has a total acrylamide content, T (T=total concentration of acrylamide and bisacrylamide monomer), ranging from 1 to 20% T, such as from 1 to 15% T, including from 1 to 10% T, for example from 3 to 7% T. In some instances, the separation medium has a total acrylamide content of 5% T. In certain cases, the separation medium may include a polyacrylamide gel that has a cross-linker concentration, C (C=concentration of cross-linker), ranging from 1 to 10% C, such as from 1 to 7% C, including from 1 to 5% C. In some instances, the separation medium has a cross-linker concentration of 3% C.

In certain embodiments, the separation medium includes a buffer. The buffer may be any convenient buffer used for gel electrophoresis. In certain embodiments, the separation medium includes a buffer, such as a Tris-glycine buffer. For example, the buffer may include a mixture of Tris and glycine. Other buffers may also be used as desired, such as, but not limited to, a tricine-arginine buffer, and the like.

In some cases, the buffer includes a detergent. In certain instances, the detergent is configured to provide analytes in the sample with substantially similar charge-to-mass ratios. Analytes with substantially similar charge-to-mass ratios may facilitate the separation of the analytes into one or more bands in the separation medium based on the molecular masses of the analytes in the sample. Certain embodiments of the buffer may include an anionic detergent. In certain cases, the detergent is an anionic detergent configured to provide analytes in the sample with a negative charge. For instance, the detergent may be an anionic detergent, such as, but not limited to, sodium dodecyl sulfate (SDS). In certain cases, the detergent is a cationic detergent configured to provide analytes in the sample with a charge, such as a positive charge. For example, the detergent may be a cationic detergent configured to provide analytes in the sample with a positive charge. In some embodiments, the cationic detergent is cetyltrimethylammonium bromide (CTAB), also known as cetrimonium bromide or hexadecyltrimethylammonium bromide.

Protein Renaturation Component

As summarized above, embodiments of the present disclosure include microfluidic devices that include a protein renaturation component. By protein renaturation component is meant an element or portion of the device which functions to renature a protein from a denatured state, e.g., to refold a protein so that the tertiary structure is restored. Any convenient protein renaturation component may be employed. For example, protein renaturation can be based on differential migration and diffusion, dialysis, dilution, size exclusion membranes, filters, ion exchange materials or columns, a renaturing buffer or other refolding related chemicals. In some embodiments, the protein renaturation component is configured to contact a denatured protein with a renaturing reagent. Contacting a denatured protein with a renaturing reagent may facilitate the renaturation of the protein. In certain instances, the renaturation component is configured to remove a denaturing reagent associated with the denatured protein. Removing a previously associated denaturing reagent from the denatured protein may allow the protein to renature.

In some instances, the renaturation component is configured to remove a denaturing reagent, such as detergent molecules, associated with the protein, where prior association of the detergent molecules with the protein resulted in denaturation of the protein. As such, in some instances the renaturation component is configured to separate detergent molecules from proteins in protein-detergent molecule complexes so that the protein can be renatured, e.g., in terms of its tertiary structure being restored. In some instances, restoration of tertiary structure is accompanied by a restoration of activity of the protein.

In certain embodiments, the protein renaturation component is configured to remove a denaturing reagent associated with the protein based on differential migration and diffusion, dialysis, dilution, size exclusion membranes, filters, ion exchange materials or columns. In some cases, the protein renaturation component is a protein renaturation membrane. The protein renaturation membrane may be configured to remove detergent molecules associated with the protein. For example, the membrane may be a size-exclusion membrane. The size-exclusion membrane may be configured to separate components in the sample based on their size as the sample flows through the membrane. In certain cases, the size-exclusion membrane is configured to separate high molecular mass components in a sample from low molecular mass components in the sample. For instance, the size-exclusion membrane may have a pore size configured to retain components in a sample (e.g., proteins) that have a size greater than the pore size of the membrane, such that these larger-sized components do not substantially pass through the membrane, and to allow components with a size below the pore size (e.g., detergent molecules) to pass through the membrane and be washed away from the proteins retained by the membrane. In certain cases, the pore size of the membrane is between the sizes of the detergent molecules and the proteins in the sample, such that the average size of the detergent molecules less than the pore size of the membrane and the average size of the proteins in the sample is greater than the pore size of the membrane. Embodiments of the renaturation membrane may also be configured to separate proteins from other small molecules, such as free dyes and salts.

In certain instances, the membrane is a sub-nanopore gel membrane. By "sub-nanopore" is meant that the membrane has pores with a nanometer-scale pore size or smaller. The sub-nanopore gel membrane has, in some embodiments, pores having a size that is sufficient to allow passage of small detergent molecules, e.g., molecules having a molecular mass of 1000 Daltons or less, such as 500 Daltons or less, or 300 Daltons or less, but inhibit passage of larger molecules, such as molecules having a molecular mass of 5000 Daltons or more, such as 10,000 Daltons or more, including 100,000 Daltons or more. While the structure of this membrane may vary, in some instances, the membrane is one that has been polymerized from a precursor having a monomer (e.g., acrylamide) concentration that is sufficient to provide for the desired pore size, where the monomer concentration may be 30% T or greater, or 35% T or greater, or 40% T or greater, such as 45% T or greater, e.g., 50% T or greater. In some instances, the monomer concentration ranges from 40 to 50% T, such as 45% T. The concentration of cross-linker may also vary, and in some instances may be 1% C or greater, or 2% C or greater, such as 3% C or greater, including 4% C or greater, e.g., 5% C or greater, such as 7% C or greater, or 10% C or greater. In certain cases, the concentration of cross-linker ranges from 1 to 10% C, such as 5% C. Any convenient monomer and cross-linker may be employed, including but not limited to those described in PCT Application serial Nos. PCT/US2010/035314 and PCT/US2010/058590, the disclosures of each of which are herein incorporated by reference in their entirety.

Binding Medium

Aspects of the microfluidic devices include a binding medium. In certain embodiments, the binding medium may be configured to bind to and retain an analyte of interest. In some instances, an analyte bound to the binding medium facilitates detection of the analyte. The binding medium may be configured to bind to an analyte of interest based on one or more of a variety of binding interactions between the binding medium and the analyte of interest in the sample, such as, but not limited to, covalent bonds, ionic bonds, electrostatic interactions, hydrophobic interactions, hydrogen bonds, van der Waals forces (e.g., London dispersion forces), dipole-dipole interactions, combinations thereof, and the like.

In certain cases, the binding medium includes a polymer, such as a polymeric gel or polymeric monolith. By monolith is meant a single, contiguous structure. Monoliths may include a single region with the same physical and chemical composition, or may include two or more regions that differ in terms of their physical and chemical compositions. The polymeric gel may be a gel suitable for gel electrophoresis. The polymeric gel may include, but is not limited to, a polyacrylamide gel, an agarose gel, and the like. The polymeric gel may include polymers, such as, but is not limited to, acrylate polymers, alkylacrylate polymers, alkyl alkylacrylate polymers, copolymers thereof, and the like. In some cases, the binding medium may include a polyacrylamide gel that has a total acrylamide content, T, ranging from 1 to 20% T, such as from 1 to 15% T, including from 1 to 10% T, for example from 3 to 7% T. In some instances, the binding medium has a total acrylamide content of 5% T. In certain cases, the binding medium includes a polyacrylamide gel that has a cross-linker concentration, C, ranging from 1 to 10% C, such as from 1 to 7% C, including from 1 to 5% C. In some instances, the separation medium has a cross-linker concentration of 3% C.

In certain embodiments, the binding medium includes a binding member. The binding member may be configured to bind to and retain an analyte of interest in a sample. For example, the binding member may be configured to specifically bind to an analyte in the sample, such as specifically binding to a protein in the sample. In certain embodiments, the binding member is stably associated with a support. By "stably associated" is meant that, under standard conditions, a moiety is bound to or otherwise associated with another moiety or structure. In certain instances, the support is a polymeric gel, as described above. As such, in certain embodiments, the microfluidic devices include both a binding medium and a binding member, as described herein. Bonds between the binding member and the support may include covalent bonds and non-covalent interactions, such as, but not limited to, ionic bonds, electrostatic interactions, hydrophobic interactions, hydrogen bonds, van der Waals forces (e.g., London dispersion forces), dipole-dipole interactions, and the like. In certain embodiments, the binding member may be covalently bound to the support, such as cross-linked or copolymerized to the support. For example, the binding member may be bound to the support through a linking group, such as, but not limited to: a receptor/ligand binding pair; a ligand-binding portion of a receptor; an antibody/antigen binding pair; an antigen-binding fragment of an antibody; a hapten; a lectin/carbohydrate binding pair; an enzyme/substrate binding pair; a biotin/avidin binding pair; a biotin/streptavidin binding pair; a digoxin/antidigoxin binding pair; a DNA or RNA aptamer binding pair; a peptide aptamer binding pair; and the like. In some cases, the binding member is bound to the support through a biotin/streptavidin or a biotin/avidin binding pair. As described above, the support-bound binding member may be configured to specifically bind to the analyte of interest. As such, specific binding of the analyte of interest to the support-bound binding member may indirectly bind the analyte of interest to the support. Binding of the analyte of interest to the support may stably associate the analyte with the support and thus facilitate detection of the analyte of interest.

A binding member can be any molecule that specifically binds to a protein, sugar, nucleic acid sequence or biomacromolecule that is being targeted (e.g., the analyte of interest). Depending on the nature of the analyte, binding members can be, but are not limited to, (a) antibodies against an epitope of a peptidic analyte for the detection of proteins and peptides; (b) a lectin that specifically binds to sugar or carbohydrate moieties on glycosylated proteins; (c) single stranded DNA complementary to a unique region of a target DNA or RNA sequence for the detection of nucleic acids; or (d) any recognition molecule, such as a member of a specific binding pair. For example, suitable specific binding pairs include, but are not limited to: a member of an antibody/antigen pair; a member of a lectin/carbohydrate pair; a receptor/ligand pair; a ligand-binding portion of a receptor; an antigen-binding fragment of an antibody; a hapten; a member of an enzyme/ substrate pair; biotin/avidin; biotin/streptavidin; digoxin/antidigoxin; a member of a DNA or RNA aptamer binding pair; a member of a peptide aptamer binding pair; and the like.

In some instances, the binding member is a proteinaceous binding member. For example, the binding member may be composed of amino acids to form a peptide-based or protein-based binding member. In some embodiments, the proteinaceous binding member may specifically bind to a protein, sugar, nucleic acid sequence, biomacromolecule, etc. that is being targeted. For instance, the proteinaceous binding member may include, but is not limited to, an antibody, an antibody fragment, a lectin, and the like. In certain embodiments, the proteinaceous binding member is an antibody or a fragment thereof. The antibody or antibody fragment may specifically bind to an antigen on the analyte of interest. In certain embodiments, the proteinaceous binding member is a lectin. The lectin may specifically bind to one or more sugars or carbohydrates, such as a glycosylated portion of a target protein.

In certain embodiments, two or more different binding members are stably associated with the binding medium. The two or more different binding members may specifically bind to the same or different analytes. In some cases, the two or more different binding members may specifically bind to the same analyte. For instance, the two or more different binding members may include different antibodies specific for different epitopes on the same analyte. In other cases, the two or more different binding members may specifically bind to different analytes. For example, the two or more binding members may include different antibodies specific for epitopes on different analytes, or different lectins specific for different sugars or sugar derivatives. Each type of binding member may be bound to the same region of the binding medium, or to different regions within the binding medium. In some cases, each type of binding member is bound to different regions in the binding medium. For example, in embodiments that include the binding medium in side channels of the microfluidic device, each side channel may include a different binding member. Embodiments that have different binding members bound to different regions in the binding medium may facilitate the detection of different analytes in the sample, where each different analyte is bound to its corresponding binding member in different regions of the binding medium.

As described above, the binding medium may include a binding member that specifically binds to an analyte of interest. Analytes not of interest are not bound by the binding member and may traverse the binding medium without binding to the binding member. In certain embodiments, the analytes not of interest that traverse the binding medium without binding to the binding medium may be transferred away from the binding medium. In some cases, the device is configured to direct the analytes not of interest to a waste reservoir. In some cases, the device is in fluid communication with a secondary analysis device, such that the device is configured to direct the analytes that pass through the binding medium without binding to the binding member to the secondary analysis device for further analysis. The secondary analysis device may include, but is not limited to, a UV spectrometer, and IR spectrometer, a mass spectrometer, an HPLC, an affinity assay device, and the like. In some instances, the secondary analysis device is included on the same substrate as the microfluidic device. In these embodiments, the microfluidic device and the secondary analysis device may be provided on a single substrate for the analysis of a sample by one or more different analysis techniques. In certain embodiments, the secondary analysis device is included as part of a system, where the system includes a microfluidic device and one or more separate secondary analysis devices. As described above, the microfluidic device and the secondary analysis device may be in fluid communication with each other, such that analytes that pass through the microfluidic device may be directed to the secondary analysis device for further characterization of the analytes.

In certain embodiments, the binding medium is a pan-capture binding medium. By "pan-capture" is meant that the binding medium non-specifically binds to analytes in a sample. For example, a pan-capture binding medium may non-specifically bind to proteins in a sample. Non-specific binding may include binding to substantially all of the analytes in a sample. In some cases, non-specific binding is based on a binding interaction between the analytes in a sample and the pan-capture binding medium. The binding interaction can be based on one or more of a variety of binding interactions between the pan-capture binding medium and the analytes in the sample, such as, but not limited to, covalent bonds, ionic bonds, electrostatic interactions, hydrophobic interactions, hydrogen bonds, van der Waals forces (e.g., London dispersion forces), dipole-dipole interactions, combinations thereof, and the like. The binding interactions may be substantially permanent (e.g., requiring a relatively large amount of energy to overcome the binding interaction, such as with covalent bonds) or may be reversible (e.g., requiring a relatively low amount of energy to disrupt the binding interaction, such as with dipole-dipole interactions).

In certain embodiments, the pan-capture binding medium is configured to non-specifically bind to analytes in the sample through electrostatic interactions. In some cases, electrostatic interactions include binding interactions due to the attraction between two oppositely charged ions. For example, electrostatic interactions may be present between a positively charged analyte and a negatively charged binding medium. Similarly, electrostatic interactions may be present between a negatively charged analyte and a positively charged binding medium. In certain instances, the binding medium is configured to have a negative charge. As such, the negatively charged binding medium may be configured to have electrostatic binding interactions with positively charged analytes. In other instances, the binding medium is configured to have a positive charge. As such, the negatively charged binding medium may be configured to have electrostatic binding interactions with positively charged analytes. Additional aspects of the pan-capture binding medium and buffers, detergents and other reagents useful with such pan-capture binding media are found in U.S. application Ser. No. 13/303,047, filed Nov. 22, 2011, the disclosure of which is incorporated by reference herein in its entirety.

Further Aspects of Embodiments of the Microfluidic Devices

Aspects of the microfluidic devices include embodiments where the separation medium is in fluid communication with the protein renaturation component (e.g., sub-nanopore gel membrane). The microfluidic device may be configured to direct a sample through the separation medium first to produce a separated sample. In certain embodiments, the microfluidic device is configured such that the separation medium and the renaturation component are in direct fluid communication with each other, such that the renaturation component is in electrophoretic communication with the separation medium. For example, the separation medium may be in direct contact with the renaturation component. In some cases, the separation medium and the renaturation component are bound to each other, such as contiguously photopatterned side-by-side. Embodiments where the separation medium is in direct fluid communication with the renaturation component may facilitate the transfer of sample components from the separation medium to the renaturation component with a minimal loss of sample components. In some instances, the microfluidic devices are configured such that sample components are quantitatively and reproducibly transferred from the separation medium to the renaturation component.

In certain embodiments, the microfluidic device is configured to direct the separated sample from the separation medium to the renaturation component. In some cases, the microfluidic device is configured such that the separation medium and the renaturation component are in direct fluid communication with each other, such that a sample or analyte can traverse directly from the separation medium to the renaturation component. As described above, the renaturation component may be configured to subject proteins in the separated sample to renaturing conditions. For example, the renaturation component may be configured to retain proteins in the separated sample that have an average size greater than the pore size of the renaturation membrane, while allowing sample components (e.g., detergent molecules) that have an average size smaller than the pore size of the renaturation membrane to pass through the renaturation membrane. In some cases, removal of the detergent molecules (e.g., SDS) from the proteins in the sample facilitates the renaturation of the proteins.

In some instances, the separation medium is also in fluid communication with the binding medium. In certain embodiments, the microfluidic device is configured such that the separation medium and the binding medium are in direct fluid communication with each other, such that the binding medium is in electrophoretic communication with the separation medium. For example, the separation medium may be in direct contact with the binding medium. In some cases, the separation medium and the binding medium are bound to each other, such as contiguously photopatterned side-by-side. In some instances, the microfluidic device is configured to direct the renatured sample from the renaturation component to the binding medium. For instance, the device may be configured such that the renaturation component bounds a first side of the separation medium and the binding medium bounds a second side of the separation medium that is opposite the first side. Embodiments where the separation medium is in direct fluid communication with both the renaturation component and the binding medium may facilitate the transfer of sample components from the separation medium to the renaturation component and from the renaturation component to the binding medium with a minimal loss of sample components during transfer. In some instances, the microfluidic device is configured such that sample components are quantitatively and reproducibly transferred from the separation medium to the renaturation component and from the renaturation component to the binding medium.

In certain embodiments, the microfluidic devices are multi-directional microfluidic devices. By "multi-directional" is meant more than one direction, such as two or more directions, three or more directions, four or more directions, etc. In certain cases, two or more directions are included in a single plane, such that the two or more directions are co-planar. In some instances, the microfluidic devices are configured to direct a fluid in more than one direction (e.g., the microfluidic devices are multi-directional), such as two or more directions, three or more directions, four or more directions, etc. In some instances, the microfluidic device is included in a substrate, such that the microfluidic device is planar. The microfluidic device may be configured to direct fluids in multiple directions within that plane.

Aspects of the microfluidic devices include a separation medium having a first (e.g., separation) flow path and a renaturation component in fluid communication with the separation medium. The separation medium may include a first flow path with a first directional axis, which corresponds to the direction the sample travels as the sample traverses the separation medium. The renaturation component may have a second flow path with a second directional axis. In some instances, the second flow path is the direction the sample travels as the sample traverses from the separation medium to the renaturation component (e.g., the renaturation membrane). Sample components smaller than the pore size of the renaturation membrane may traverse the renaturation membrane in the direction of the second flow path. For instance, small molecular mass sample components, such as detergent molecules may traverse (e.g., pass through) the renaturation membrane. Sample components larger than the pore size of the renaturation membrane may be retained by the renaturation membrane. For example, large molecular mass sample components, such as proteins may be retained by the renaturation membrane.

The renaturation component may have a directional axis different from the directional axis of the separation medium. In some cases, the first directional axis of the separation medium is aligned in a different direction from the second directional axis of the renaturation component. In cases where the first directional axis is aligned in a different direction from the second directional axis, the microfluidic devices are multi-dimensional (e.g., multi-directional) microfluidic devices, as described above. For example, the second directional axis may be at an angle of 180 degrees or less with respect to the first directional axis, such as 150 degrees of less, 135 degrees or less, including 120 degrees or less, 90 degrees or less, 60 degrees or less, 45 degrees or less, or 30 degrees or less with respect to the first directional axis. In certain embodiments, the second directional axis is orthogonal to the first directional axis.

In certain embodiments, the binding medium has a third (e.g., labeling) flow path with a directional axis. In some instances, the third flow path is the direction the sample travels as the sample or analyte traverses from the renaturation component to the binding medium. The binding medium may have a flow path with a directional axis the same as, or different from the flow path of the renaturation component. For example, as described above, the protein renaturation component may have a flow path with a second directional axis. In certain instances, the binding medium may have flow path with a directional axis aligned with or substantially parallel to the second directional axis of the protein renaturation component. In some cases, the flow path of the renaturation component and the flow path of the binding medium are aligned along the same directional axis, but have opposite flow directions. For instance, the renaturation component may have a flow path aligned along the second directional axis with a first flow direction, and the binding medium may have a flow path also aligned along the second directional axis but with a flow direction having a direction opposite the first flow direction. As described above, the device may be configured such that the renaturation component bounds a first side of the separation medium and the binding medium bounds a second side of the separation medium that is opposite the first side. In these embodiments, the device may be configured to direct a sample from the separation medium towards the renaturation component along the second directional axis, and then towards the binding medium in an opposite direction along the same second directional axis.

In some instances, the microfluidic device is configured to subject a sample to two or more directionally distinct flow fields. By "flow field" is meant a region where components traverse the region in substantially the same direction. For example, a flow field may include a region where mobile components move through a medium in substantially the same direction. A flow field may include a region, such as a separation medium, a renaturation component, a binding medium, a loading medium, etc., where components, such as buffers, analytes, reagents, etc., move through the region in substantially the same direction. A flow field may be induced by an applied electric field, a pressure differential, electroosmosis, and the like. In some embodiments, the two or more flow fields may be directionally distinct. For example, a first flow field may be aligned with the directional axis of the separation flow path of the separation medium. The first flow field may be configured to direct the sample or analytes through the separation medium along the separation flow path. A second flow field may be aligned with the directional axis of the flow path of the renaturation component. In some instances, the second flow field is configured to direct the sample or analytes from the separation medium to the renaturation component along the flow path of the renaturation component. For example, the second flow field may be configured to direct the proteins separated by the separation medium to the renaturation component while maintaining substantially the same separation of the proteins. The second flow field may be configured to direct the sample or analytes from the separation medium to the renaturation component such that proteins in the sample contact and are retained by the renaturation component. As described above, in certain instances, the directional axis of the renaturation component flow path is orthogonal to the directional axis of the separation flow path. In these instances, the second flow field may be orthogonal to the first flow field.

In some instances, the device is configured to subject the sample to a third flow field. The third flow field may be aligned with the directional axis of the flow path of the binding medium. In certain cases, this directional axis is aligned with or substantially parallel to the directional axis of the renaturation component. In some instances, the third flow field is configured to direct the sample or analytes from the renaturation component to the binding medium along the flow path of the binding medium. For example, the third flow field may be configured to direct the proteins separated by the separation medium and renatured by the renaturation component to the binding medium while maintaining substantially the same separation of the proteins. The third flow field may be configured to direct the sample or analytes from the renaturation component to the binding medium such that one or more analytes of interest in the sample contact and bind to the binding medium. As described above, in certain instances, the directional axis of the binding medium flow path is parallel to the directional axis of the renaturation component flow path. In these instances, the third flow field may be parallel, but in an opposite direction to the second flow field.

In certain embodiments, the microfluidic device is configured to subject a sample to two or more directionally distinct electric fields. The electric fields may facilitate the movement of the sample through the microfluidic device (e.g., electrokinetic transfer of the sample from one region of the microfluidic device to another region of the microfluidic device). The electric fields may also facilitate the separation of the analytes in the sample by electrophoresis (e.g., polyacrylamide gel electrophoresis (PAGE)), as described above. For instance, the electric field may be configured to direct the analytes in a sample through the separation medium of the microfluidic device. The electric field may be configured to facilitate the separation of the analytes in a sample based on the physical properties of the analytes. For example, the electric field may be configured to facilitate the separation of the analytes in the sample based on the molecular mass, size, charge (e.g., charge to mass ratio), isoelectric point, etc. of the analytes. In certain instances, the electric field is configured to facilitate the separation of the analytes in the sample based on the molecular mass of the analytes.

In some embodiments, the two or more electric fields may be directionally distinct. For example, a first electric field may be aligned with the directional axis of the separation flow path of the separation medium. The first electric field may be configured to direct the sample or analytes through the separation medium along the separation flow path. A second electric field may be aligned with the directional axis of the flow path of the renaturation component. In some instances, the second electric field is configured to direct the sample or analytes from the separation medium to the renaturation component along the flow path of the renaturation component. The second electric field may be configured to direct the analytes from the separation medium to the renaturation component such that proteins in the sample contact and are retained by the renaturation component. As described above, in certain instances, the directional axis of the renaturation component flow path is orthogonal to the directional axis of the separation flow path. In these instances, the second electric field may be orthogonal to the first electric field.

In certain embodiments, a third electric field may be aligned with the directional axis of the flow path of the binding medium. In some instances, the third electric field is configured to direct the sample or analytes from the renaturation component to the binding medium along the flow path of the binding medium. The third electric field may be configured to direct the analytes from the renaturation component to the binding medium such that the analytes contact and bind to the binding medium. As described above, in certain instances, the directional axis of the binding medium flow path is parallel to the directional axis of the renaturation component flow path. In these instances, the third electric field may be parallel, but in an opposite direction to the second electric field.

In certain embodiments, the microfluidic device includes one or more electric field generators configured to generate an electric field. The electric field generator may be configured to apply an electric field to various regions of the microfluidic device, such as one or more of the separation medium, the renaturation component, the binding medium, the loading medium, and the like. For example, the electric field generator may be configured to apply an electric field to a microfluidic channel of the microfluidic device, such as one or more microfluidic side channels of the device. The electric field generator may be configured to electrokinetically transport the analytes and components in a sample through the various media in the microfluidic device. In certain instances, the electric field generator may be proximal to the microfluidic device, such as arranged on the microfluidic device. In some cases, the electric field generator is positioned a distance from the microfluidic device. For example, the electric field generator may be incorporated into a system for detecting an analyte, as described in more detail below.

Embodiments of the microfluidic device may be made of any suitable material that is compatible with the assay conditions, samples, buffers, reagents, etc. used in the microfluidic device. In some cases, the microfluidic device is made of a material that is inert (e.g., does not degrade or react) with respect to the samples, buffers, reagents, etc. used in the subject microfluidic device and methods. For instance, the microfluidic device may be made of materials, such as, but not limited to, glass, quartz, polymers, elastomers, paper, combinations thereof, and the like.

In some instances, the microfluidic device includes one or more sample input ports. The sample input port may be configured to allow a sample to be introduced into the microfluidic device. The sample input port may be in fluid communication with the separation medium. In some instances, the sample input port is in fluid communication with the upstream end of the separation medium. The sample input port may further include a structure configured to prevent fluid from exiting the sample input port. For example, the sample input port may include a cap, valve, seal, etc. that may be, for instance, punctured or opened to allow the introduction of a sample into the microfluidic device, and then re-sealed or closed to substantially prevent fluid, including the sample and/or buffer, from exiting the sample input port.

In certain embodiments, the microfluidic device is substantially transparent. By "transparent" is meant that a substance allows visible light to pass through the substance. In some embodiments, a transparent microfluidic device facilitates detection of analytes bound to the binding medium, for example analytes that include a detectable label, such as a fluorescent label. In some cases, the microfluidic device is substantially opaque. By "opaque" is meant that a substance does not allow visible light to pass through the substance. In certain instances, an opaque microfluidic device may facilitate the analysis of analytes that are sensitive to light, such as analytes that react or degrade in the presence of light.

In some aspects, the separation medium and the binding medium are provided in a single common chamber, as illustrated in FIG. 1. In these embodiments, the microfluidic device includes a chamber. The chamber may include a loading medium, a separation medium, a renaturation component, and a binding medium. As described above, the separation medium may be in fluid communication, such as in direct physical contact, with the renaturation component and the binding medium. In some cases, the separation medium is bound to the renaturation component and the binding medium, such as contiguously photopatterned side-by-side to renaturation component and the binding medium. As such, the chamber may be configured to contain both the separation medium, the renaturation component and the binding medium in fluid communication with each other.

In addition to the separation medium, the renaturation component and the binding medium, the chamber may also include a loading medium. The loading medium may be in fluid communication with the separation medium. In some instances, the loading medium is in direct physical contact with the separation medium, such that the loading medium in in electrophoretic communication with the separation medium. For example, the loading medium may be bound to the separation medium, such as contiguously photopatterned side-by-side. The loading medium may be positioned such that the sample contacts the loading medium before contacting the separation medium. For instance, the loading medium may bound one side of the separation medium. As described above, the microfluidic device may be configured such that the renaturation component bounds a first side of the separation medium and the binding medium bounds a second side of the separation medium that is opposite the first side. In these embodiments, the loading medium may bound a third side of the separation medium between the first and second sides. In certain embodiments, the loading medium facilitates contacting a sample with the separation medium. For instance, the loading medium may be configured to concentrate the sample before the sample contacts the separation medium. In certain embodiments, the loading medium may include two or more regions that have different physical and/or chemical properties. The loading medium may include a loading region and a stacking region. The loading medium may be configured to include a loading region upstream from a stacking region. In certain embodiments, the loading medium includes a polymer, such as a polymeric gel. The polymeric gel may be a gel suitable for gel electrophoresis. The polymeric gel may include, but is not limited to, a polyacrylamide gel, an agarose gel, and the like. In some cases, the loading region includes a polymeric gel with a large pore size. For example, the loading region may include a polyacrylamide gel that has a total acrylamide content of 5% T or less, such as 4% T or less, including 3% T or less, or 2% T or less. In some instances, the loading region has a total acrylamide content of 3% T. The loading region may include a cross-linker that has a cross-linker concentration of 5% C or less, such as 4% C or less, including 3% C or less, or 2% C or less. In some instances, the loading region has a cross-linker concentration of 3% C. In some cases, the stacking region of the loading medium may be configured to concentrate the sample before the sample contacts the separation medium. The stacking region may include a polymeric gel with a smaller pore size than the loading region. For example, the stacking region may include a polyacrylamide gel that has a total acrylamide content of ranging from 1% to 10%, such as from 1% to 7%, including from 3% to 7%. In some instances, the stacking region has a total acrylamide content of 5%. The smaller pore size of the stacking region may slow the electrophoretic movement of the sample through the stacking region, thus concentrating the sample before it contacts the separation medium.

In certain instances, the chamber contains the loading medium, the separation medium, the renaturation component and the binding medium. The chamber may be configured to contain the loading medium, the separation medium, the renaturation component and the binding medium such that the loading medium, the separation medium, the renaturation component and the binding medium are in fluid communication with each other, as described above. For example, the chamber may include a contiguous polymeric gel monolith with various regions. Each region of the contiguous polymeric gel monolith may have different physical and/or chemical properties. The contiguous polymeric gel monolith may include a first region having a loading medium, a second region having a separation medium, a third region having a renaturation component and a fourth region having a binding medium. The flow paths of each region of the polymeric gel monolith may be configured such that a sample first contacts the loading medium, then contacts the separation medium, then contacts the renaturation component, and finally contacts the binding medium.

In some embodiments, the chamber is configured with one or more arrays of side channels. For example, the chamber may include a first array of side channels in fluid communication with a first side of the chamber, and a second array of side channels in fluid communication with a second side of the chamber. In some cases, the first array of side channels is opposite the second array of side channels. Each array of side channels may include a plurality of individual channels (e.g., two or more individual channels) that are each in fluid communication with the chamber. For instance, each array of side channels may include 2 or more, 4 or more, 6 or more, 8 or more, 10 or more, 15 or more, 20 or more, 25 or more, 50 or more, 100 or more, etc., individual side channels. Each side channel may have a width of 100 µm or less, such as 75 µm or less, including 50 µm or less, for instance 25 µm or less, etc.

The spacing between each side channel may vary, and in some embodiments is 200 µm or less, such as 100 or less, including 50 µm or less, or 10 µm or less.

Each array of side channels may contain different regions of the microfluidic device, as described above. For example, a first array of side channels may include a renaturation component. In these embodiments, the side channels in the first array may each include the renaturation component, such that the renaturation component is contained in the side channels of the first array. In some instances, the microfluidic device includes a second array of side channels. The second array of side channels may include a binding medium. In these embodiments, the side channels in the second array may each include the binding medium, such that the binding medium is contained in the side channels of the second array. In the configuration described above, the renaturation component is contained in the first array of side channels and the binding medium is contained in the second array of side channels. The first and second arrays of side channels may be configured on opposite sides of the chamber, as described above. As such, the chamber configured between the first and second arrays of side channels may contain the loading medium and the separation medium, with the renaturation component and the binding medium contained in the first and second arrays of side channels, as described above.

Examples of different types of regions and configurations for the microfluidic devices are further described in PCT Application serial Nos. PCT/US2010/035314 and PCT/US2010/058590, the disclosures of each of which are herein incorporated by reference in their entirety.

FIG. 1(a) shows a photograph of a microfluidic device 10. As shown in FIG. 1(a), the microfluidic device 10 includes a chamber 11. The microfluidic device 10 also includes various microfluidic channels, such as inlet channels 1, 2, and 3, and control channels 4, 5, 6, 7, and 8. Each microfluidic channel has a corresponding access port.

Figure 2:
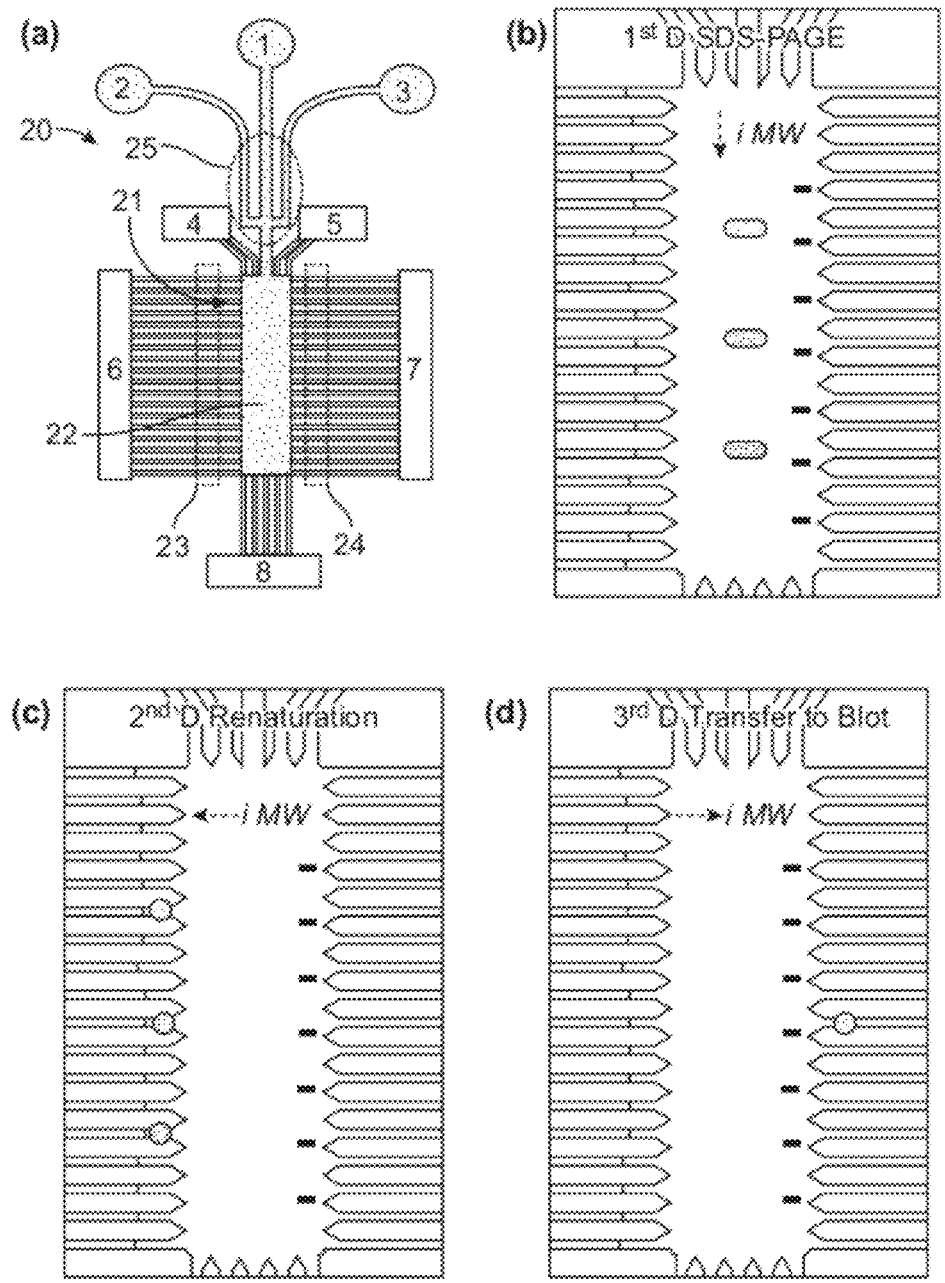
FIG. 2(a) shows a schematic of a microfluidic device for multi-dimensional operation, including an injector for sample loading, rectangular chamber for separation, left side channels for renaturation, and right side channels for binding (e.g., blotting), according to embodiments of the present disclosure.
FIGS. 2(b)-2(d) show images overlaid with schematics of a microfluidic Western blotting protocol with in-situ protein renaturation, according to embodiments of the present disclosure.

FIG. 2(a) shows a schematic of a microfluidic device 20 that includes a chamber 21 that contains a separation medium 22. The separation medium 22 is in fluid communication with a first array of side channels 23, which contains the renaturation component, and a second array of side channels 24, which contains the binding medium. The first array of side channels 23 is arranged on a first side of the chamber 21, and the second array of side channels 24 is arranged on an opposite side of the chamber 21. The microfluidic device 20 also includes various microfluidic channels, such as inlet channels 1, 2, and 3, and control channels 4, 5, 6, 7, and 8. Inlet channels 1, 2, and 3 may be configured to direct a fluid sample into the chamber 21. Control channels 4, 5, 6, 7, and 8 may be configured to direct fluids (e.g., reagents, labels, buffers, wash fluids, etc.) into and/or away from the chamber 21. In addition, control channels 4, 5, 6, 7, and 8 may be configured to apply an electric field to various regions of the microfluidic device for electrokinetically transporting analytes in a sample through the separation medium 22, the renaturation component and the binding medium.

Methods

Embodiments of the methods are directed to determining whether an analyte is present or absent in a sample, e.g., determining the presence or absence of one or more analytes in a sample. In certain embodiments of the methods, the presence of one or more analytes in the sample may be determined qualitatively or quantitatively. Qualitative determination includes determinations in which a simple yes/no result with respect to the presence of an analyte in the sample is provided to a user. Quantitative determination includes both semi-quantitative determinations in which a rough scale result, e.g., low, medium, high, is provided to a user regarding the amount of analyte in the sample and fine scale results in which an exact measurement of the concentration of the analyte is provided to the user.

In certain embodiments, the microfluidic devices are configured to detect the presence or absence of one or more analytes in a sample. The method includes introducing a fluid sample into a microfluidic device. Introducing the fluid sample into the microfluidic device may include contacting the sample with the separation medium, or in embodiments of the microfluidic devices that include a loading medium, contacting the sample with the loading medium. The method further includes directing the sample through the separation medium to produce a separated sample. In some cases, the separated sample is produced by gel electrophoresis as the sample traverses the separation medium, as described above. The separated sample may include distinct detectable bands of analytes, where each band includes one or more analytes that have substantially similar properties, such as molecular mass, size, charge (e.g., charge to mass ratio), isoelectric point, etc. depending on the type of gel electrophoresis performed.

Aspects of the methods may also include transferring the separated sample to a renaturation component. In some embodiments, the method includes transferring the entire separated sample to the renaturation component. In other cases, specific bands of analytes in the separated sample may be selectively transferred to the renaturation component. In certain embodiments, the method also includes renaturing separated proteins in the sample. Renaturing the separated proteins may include contacting the separated proteins with a renaturation component of the microfluidic device. As described above, the renaturation component may include a sub-nanopore gel membrane. In some cases, renaturing the proteins in the sample includes separating the proteins from denaturing agents, such as detergents (e.g., SDS). The denaturing agents and/or detergents may be washed away from the proteins retained by the renaturation membrane by flowing a buffer or other wash fluid through the sample retained by the renaturation membrane. Components with average sizes smaller than the pore size of the membrane (e.g., detergent molecules) may be washed away from components with average sizes larger than the pore size of the membrane (e.g., proteins).

Aspects of the methods may also include transferring the renatured sample to a binding medium. In some embodiments, the method includes transferring the entire renatured sample to the binding medium. In other cases, specific bands of analytes in the renatured sample may be selectively transferred to the binding medium. In some cases, the method includes contacting the analytes in the renatured sample with the binding medium. As described above, the binding medium may be configured to specifically bind to analytes, thus retaining the analytes of interest in the binding medium. In some instances, the method includes transferring the renatured sample to the binding medium, where the transferring includes contacting the sample to a proteinaceous binding member bound to the binding medium. As described above, the proteinaceous binding member may include an antibody or a fragment thereof (e.g., a fragment of an antibody). In some cases, the proteinaceous binding member includes a lectin.

In certain embodiments, the method includes detecting an analyte of interest bound to the binding medium. Detectable binding of an analyte of interest to the binding medium indicates the presence of the analyte of interest in the sample. Analytes not of interest that traverse the binding medium and do not bind to the binding medium may be washed away or transferred to a secondary analysis device such as, but not limited to, a UV spectrometer, and IR spectrometer, a mass spectrometer, an HPLC, an affinity assay device, and the like.

In some instances, detecting the analyte of interest bound to the binding medium includes contacting the analyte of interest with a label configured to specifically bind to the analyte of interest. The label can be any molecule that specifically binds to a protein, nucleic acid sequence, biomacromolecule or a portion thereof that is being targeted (e.g., the analyte of interest). Depending on the nature of the analyte, the label can be, but is not limited to: an antibody that specifically binds an epitope of a peptidic analyte for the detection of proteins and peptides; a lectin that specifically binds a sugar or carbohydrate (e.g., for the detection of glycosylated proteins); single stranded DNA complementary to a unique region of a target DNA or RNA sequence for the detection of nucleic acids; or any recognition molecule, such as a member of a specific binding pair. For example, suitable specific binding pairs include, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. In certain embodiments, the label includes an antibody. In some cases, the label includes a lectin. The antibody or lectin may specifically bind to the analyte of interest.

In certain embodiments, the label includes a detectable label. Detectable labels include any convenient label that may be detected using the methods and systems, and may include, but are not limited to, fluorescent labels, colorimetric labels, chemiluminescent labels, multicolor reagents, enzyme-linked reagents, avidin-streptavidin associated detection reagents, radiolabels, gold particles, magnetic labels, and the like. In certain embodiments, the label includes an antibody associated with a detectable label. In some instances, the label includes a lectin associated with a detectable label. For example, the label may include a fluorescently labeled antibody or lectin that specifically binds to the analyte of interest.

Samples that may be assayed with the subject methods may include both simple and complex samples. Simple samples are samples that include the analyte of interest, and may or may not include one or more molecular entities that are not of interest, where the number of these non-interest molecular entities may be low, e.g., 10 or less, 5 or less, etc. Simple samples may include initial biological or other samples that have been processed in some manner, e.g., to remove potentially interfering molecular entities from the sample. By "complex sample" is meant a sample that may or may not have the analyte of interest, but also includes many different proteins and other molecules that are not of interest. In some instances, the complex sample assayed in the subject methods is one that includes 10 or more, such as 20 or more, including 100 or more, e.g., $10^3$ or more, $10^4$ or more (such as 15,000; 20,000 or 25,000 or more) distinct (i.e., different) molecular entities, that differ from each other in terms of molecular structure or physical properties (e.g., molecular mass, size, charge, isoelectric point, etc.).

In certain embodiments, the samples of interest are biological samples, such as, but not limited to, urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, plants, fungi, yeast, bacteria, tissue cultures, viral cultures, or combinations thereof using conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like.

As described above, the samples that may be assayed in the subject methods may include one or more analytes of interest. Examples of detectable analytes include, but are not limited to: proteins and peptides, with or without modifications, e.g., antibodies, diabodies, Fab fragments, DNA or RNA binding proteins, glycosylated proteins, phosphorylated proteins (phosphoproteomics), peptide aptamers, epitopes, and the like; nucleic acids, e.g., double or single-stranded DNA, double or single-stranded RNA, DNA-RNA hybrids, DNA aptamers, RNA aptamers, etc.; small molecules such as inhibitors, activators, ligands, etc.; oligo or polysaccharides; mixtures thereof; and the like.

In some cases, false-positive signals due to non-specific binding of the binding member to analytes not of interest are minimized. For example, non-specific binding of the binding member to analytes not of interest may be minimized and the analytes not of interest will not be detected. The analytes not of interest may traverse through the binding medium without binding to the binding medium (or to a binding member associated with the binding medium). Thus, the binding medium may specifically bind only to the analyte of interest. Specific binding of the binding medium to only the analyte of interest may facilitate the specific detection of the analyte of interest in complex samples.

In certain embodiments, the method includes concentrating, diluting, or buffer exchanging the sample prior to directing the sample through the separation medium. Concentrating the sample may include contacting the sample with a concentration medium prior to contacting the sample with the separation medium. The concentration medium may include a small pore size polymeric gel, a membrane (e.g., a size exclusion membrane), combinations thereof, and the like. Concentrating the sample prior to contacting the sample with the separation medium may facilitate an increase in the resolution between the bands of analytes in the separated sample because each separated band of analyte may disperse less as the sample traverses through the separation medium. Diluting the sample may include contacting the sample with additional buffer prior to contacting the sample with the separation medium. Buffer exchanging the sample may include contacting the sample with a buffer exchange medium prior to contacting the sample with the separation medium. The buffer exchange medium may include a buffer different from the sample buffer. The buffer exchange medium may include, but is not limited to, a molecular sieve, a porous resin, and the like.

In certain embodiments, the method includes contacting the separated analytes bound to the binding medium with a blocking reagent prior to detecting the analyte of interest. In some cases, contacting the separated analytes with a blocking reagent prior to detecting the analyte of interest may facilitate a minimization in non-specific binding of a detectable label to the separated analytes. For example, contacting the separated analytes with the blocking reagent prior to detecting the analyte of interest may facilitate a minimization in non-specific binding of a labeled antibody or a labeled lectin to the separated analytes. The blocking reagent can be any blocking reagent that functions as described above, and may include, but is not limited to, bovine serum albumin (BSA), non-fat dry milk, casein, gelatin, and the like. In certain embodiments, the method also includes optional washing steps, which may be performed at various times before, during and after the other steps in the method. For example, a washing step may be performed after transferring the separated sample from the separation medium to the renaturation component, after transferring the renatured sample from the renaturation component to the binding medium, after contacting the separated sample with the blocking reagent, after contacting the separated sample with the detectable label, etc.

Embodiments of the method may also include releasing the analyte bound to the binding medium. The releasing may include contacting the bound analyte with a releasing agent. The releasing agent may be configured to disrupt the binding interaction between the analyte and the binding medium. In some cases, the releasing agent is a reagent, buffer, or the like, that disrupts the binding interaction between the analyte and the binding medium causing the binding medium to release the analyte. After releasing the analyte from the binding medium, the method may include transferring the analyte away from the binding medium. For example, the method may include directing the released analyte downstream from the binding medium for collection or for secondary analysis with a secondary analysis device such as, but is not limited to, a UV spectrometer, and IR spectrometer, a mass spectrometer, an HPLC, an affinity assay device, and the like.

In some embodiments, the methods include the uniplex analysis of an analyte in a sample. By "uniplex analysis" is meant that a sample is analyzed to detect the presence of one analyte in the sample. For example, a sample may include a mixture of an analyte of interest and other molecular entities that are not of interest. In some cases, the methods include the uniplex analysis of the sample to determine the presence of the analyte of interest in the sample mixture.

Certain embodiments include the multiplex analysis of two or more analytes in a sample. By "multiplex analysis" is meant that the presence two or more distinct analytes, in which the two or more analytes are different from each other, is determined. For example, analytes may include detectable differences in their molecular mass, size, charge (e.g., mass to charge ratio), isoelectric point, and the like. In some instances, the number of analytes is greater than 2, such as 4 or more, 6 or more, 8 or more, etc., up to 20 or more, e.g., 50 or more, including 100 or more, distinct analytes. In certain embodiments, the methods include the multiplex analysis of 2 to 100 distinct analytes, such as 4 to 50 distinct analytes, including 4 to 20 distinct analytes. In certain embodiments, multiplex analysis also includes the use of two or more different detectable labels. The two or more different detectable labels may specifically bind to the same or different analytes. In some cases, the two or more different detectable labels may specifically bind to the same analyte. For instance, the two or more different detectable labels may include different antibodies specific for different epitopes or different lectins specific for different sugars on the same analyte. The use of two or more detectable labels specific for the same analyte may facilitate the detection of the analyte by improving the signal-to-noise ratio. In other cases, the two or more different detectable labels may specifically bind to different analytes. For example, the two or more detectable labels may include different antibodies specific for epitopes on different analytes or different lectins specific for sugars on different analytes. The use of two or more detectable labels each specific for different analytes may facilitate the detection of two or more respective analytes in the sample in a single assay.

In certain embodiments, the method is an automated method. As such, the method may include a minimum of user interaction with the microfluidic devices and systems after introducing the sample into the microfluidic device. For example, the steps of directing the sample through the separation medium to produce a separated sample and transferring the separated sample to the binding medium may be performed by the microfluidic device and system, such that the user need not manually perform these steps. In some cases, the automated method may facilitate a reduction in the total assay time. For example, embodiments of the method, including the separation and detection of analytes in a sample, may be performed in 30 min or less, such as 20 min or less, including 15 min or less, or 10 min or less, or 5 min or less, or 2 min or less, or 1 min or less.

FIGS. 1(b) and 2(b)-2(d) show schematics of an embodiment of a method for detecting the presence of an analyte in a sample. The method includes polyacrylamide gel electrophoresis (PAGE) followed by post-separation sample transfer to a renaturation component, followed by post-renaturation transfer to a binding medium and, finally, detection using a labeled antibody probe. Analytes are electrokinetically transferred from a PAGE separation medium to a contiguous renaturation component, then electrokinetically transferred to a contiguous binding medium and are identified in situ by specific affinity interactions. In step 1 (FIG. 2(b)), a sample is contacted with the separation medium and an electric field is applied along the directional axis of the separation medium to direct the sample through the separation medium, where the various analytes in the sample are separated by electrophoresis through the separation medium (FIG. 2(b)). The separation medium has a separation flow path with a first directional axis. An electric field is applied along the first directional axis (indicated by the vertical arrow) to direct the sample through the separation medium (FIG. 2(b)). The separated analytes can be transferred to the renaturation component by applying an electric field along a second directional axis (indicated by the horizontal arrow pointing to the left) to direct the separated analytes to the renaturation component (FIG. 2(c)). The renaturation component may include a sub-nanoporous membrane with a pore size larger than the average size of detergent molecules (e.g., SDS), but smaller in size than the average size of proteins in the sample (FIG. 1(b), left panel). Components with an average size smaller than the pore size of the membrane pass through the membrane, while components with an average size larger than the pore size of the membrane are retained by the membrane (FIG. 1(b), left panel). Separation of the proteins from the detergent molecules may facilitate the renaturation of the proteins. The renatured proteins can be transferred to the binding medium by applying an electric field in an opposite direction along the second directional axis (indicated by the horizontal arrow pointing to the right) to direct the renatured proteins to the binding medium (FIG. 2(d)). The binding medium includes a binding member that specifically binds to an analyte of interest (FIG. 1(b), right panel). A detectable label (e.g., a fluorescently labeled antibody) may be contacted with the analytes bound to the binding medium. The detectable label specifically binds to the analyte of interest (e.g., the target protein). A positive detection of the detectable label indicates the presence of the analyte of interest in the sample. Although the binding member in FIG. 1(b) is shown to be an antibody, other binding members may be used, such as, but not limited to, lectins, antibody fragments, oligonucleotides, and the like.

Systems

Aspects of certain embodiments include a system for detecting an analyte in a sample. In some instances, the system includes a microfluidic device as described herein. The system may also include a detector. In some cases, the detector is a detector configured to detect a detectable label. The detector may include any type of detector configured to detect the detectable label used in the assay. Detectors may be configured to evaluate a microchannel of the microfluidic device to obtain a signal from the detectable label. As described above, detectable label may be a fluorescent label, colorimetric label, chemiluminescent label, multicolor reagent, enzyme-linked reagent, avidin-streptavidin associated detection reagent, radiolabel, gold particle, magnetic label, etc. In some instances, the detectable label is a fluorescent label. In these instances, the detector may be configured to contact the fluorescent label with electromagnetic radiation (e.g., visible, UV, x-ray, etc.), which excites the fluorescent label and causes the fluorescent label to emit detectable electromagnetic radiation (e.g., visible light, etc.). The emitted electromagnetic radiation may be detected by the detector to determine the presence of the analyte bound to the binding medium.

In some instances, the detector may be configured to detect emissions from a fluorescent label, as described above. In certain cases, the detector includes a photomultiplier tube (PMT), a charge-coupled device (CCD), an intensified charge-coupled device (ICCD), a complementary metal-oxide-semiconductor (CMOS) sensor, a visual colorimetric readout, a photodiode, and the like.

Systems of the present disclosure may include various other components as desired. For example, the systems may include fluid handling components, such as microfluidic fluid handling components. The fluid handling components may be configured to direct one or more fluids through the microfluidic device. In some instances, the fluid handling components are configured to direct fluids, such as, but not limited to, sample solutions, buffers (e.g., electrophoresis buffers, wash buffers, release buffers, etc.), and the like. In certain embodiments, the microfluidic fluid handling components are configured to deliver a fluid to the separation medium of the microfluidic device, such that the fluid contacts the separation medium. The fluid handling components may include microfluidic pumps. In some cases, the microfluidic pumps are configured for pressure-driven microfluidic handling and routing of fluids through the microfluidic devices and systems disclosed herein. In certain instances, the microfluidic fluid handling components are configured to deliver small volumes of fluid, such as 1 mL or less, such as 500 µL or less, including 100 µL or less, for example 50 µL or less, or 25 µL or less, or 10 µL or less, or 5 µL or less, or 1 µL or less.

In certain embodiments, the systems include one or more electric field generators. An electric field generator may be configured to apply an electric field to various regions of the microfluidic device. The system may be configured to apply an electric field such that the sample is electrokinetically transported through the microfluidic device. For example, the electric field generator may be configured to apply an electric field to the separation medium. In some cases, the applied electric field may be aligned with the directional axis of the separation flow path of the separation medium. As such, the applied electric field may be configured to electrokinetically transport the analytes and components in a sample through the separation medium. In certain embodiments, the system includes an electric field generator configured to apply an electric field such that analytes and/or components in the sample are electrokinetically transported from the separation medium to the renaturation component. For instance, an applied electric field may be aligned with the directional axis of the flow path of the renaturation component. In some cases, the applied electric field is configured to electrokinetically transport selected analytes that have been separated by the separation medium. Analytes that have been separated by the separation medium may be transported to the renaturation component by applying an appropriate electric field along the directional axis of the flow path of the renaturation component. The electric field generators may also be configured to apply an electric field such that analytes in the sample are electrokinetically transported from the renaturation component to the binding medium. As described above, the renaturation component and the binding medium may be arranged on opposite sides of the microfluidic chamber with the flow path of the renaturation component substantially parallel to the flow path of the binding medium, but in opposite directions. As such, the renaturation component and the binding medium may use the same electric field generators, which may be configured to apply an electric field to electrokinetically transport the analytes either toward the renaturation component (e.g., away from the binding medium) or toward the binding medium (e.g., away from the renaturation component.

As described above, in certain embodiments, the microfluidic device includes one or more arrays of side channels (e.g., microfluidic channels). The electric field generators may be configured to apply the electric field to one or more of these microfluidic channels of the microfluidic device. For example, the electric field generators may be configured to apply an electric field to one or more microfluidic channels, such as control channels 4, 5, 6, 7 and 8, shown in FIG. 1(*a*). In some instances, the electric field generators are configured to apply an electric field with a strength ranging from 10 V/cm to 1000 V/cm, such as from 100 V/cm to 800 V/cm, including from 200 V/cm to 600 V/cm.

In certain embodiments, the electric field generators include voltage shaping components. In some cases, the voltage shaping components are configured to control the strength of the applied electric field, such that the applied electric field strength is substantially uniform across the separation medium and/or the binding medium. The voltage shaping components may facilitate an increase in the resolution of the analytes in the sample. For instance, the voltage shaping components may facilitate a reduction in non-uniform movement of the sample through the separation medium. In addition, the voltage shaping components may facilitate a minimization in the dispersion of the bands of analytes as the analytes traverses the separation medium.

In certain embodiments, the subject system is a biochip (e.g., a biosensor chip). By "biochip" or "biosensor chip" is meant a microfluidic system that includes a substrate surface which displays two or more distinct microfluidic devices on the substrate surface. In certain embodiments, the microfluidic system includes a substrate surface with an array of microfluidic devices.

An "array" includes any two-dimensional or substantially two-dimensional (as well as a three-dimensional) arrangement of addressable regions, e.g., spatially addressable regions. An array is "addressable" when it has multiple devices positioned at particular predetermined locations (e.g., "addresses") on the array. Array features (e.g., devices) may be separated by intervening spaces. Any given substrate may carry one, two, four or more arrays disposed on a front surface of the substrate. Depending upon the use, any or all of the arrays may be the same or different from one another and each may contain multiple distinct microfluidic devices. An array may contain one or more, including two or more, four or more, eight or more, 10 or more, 25 or more, 50 or more, or 100 or more microfluidic devices. In certain embodiments, the microfluidic devices can be arranged into an array with an area of 100 cm$^2$ or less, 50 cm$^2$ or less, or 25 cm$^2$ or less, 10 cm$^2$ or less, 5 cm$^2$ or less, such as 1 cm$^2$ or less, including 50 mm$^2$ or less, 20 mm$^2$ or less, such as 10 mm$^2$ or less, or even smaller. For example, microfluidic devices may have dimensions in the range of 10 mm×10 mm to 200 mm×200 mm, including dimensions of 100 mm×100 mm or less, such as 50 mm×50 mm or less, for instance 25 mm×25 mm or less, or 10 mm×10 mm or less, or 5 mm×5 mm or less, for instance, 1 mm×1 mm or less.

Arrays of microfluidic devices may be arranged for the multiplex analysis of samples. For example, multiple microfluidic devices may be arranged in series, such that a sample may be analyzed for the presence of several different analytes in a series of microfluidic devices. In certain embodiments, multiple microfluidic devices may be arranged in parallel, such that two or more samples may be analyzed at substantially the same time.

Aspects of the systems include that the microfluidic devices may be configured to consume a minimum amount of sample while still producing detectable results. For example, the system may be configured to use a sample volume of 100 μL or less, such as 75 μL or less, including 50 μL or less, or 25 μL or less, or 10 μL or less, for example, 5 μL or less, 2 μL or less, or 1 μL or less while still producing detectable results. In certain embodiments, the system is configured to have a detection sensitivity of 1 nM or less, such as 500 pM or less, including 100 pM or less, for instance, 1 pM or less, or 500 fM or less, or 250 fM or less, such as 100 fM or less, including 50 fM or less, or 25 fM or less, or 10 fM or less. In some instances, the system is configured to be able to detect analytes at a concentration of 1 μg/mL or less, such as 500 ng/mL or less, including 100 ng/mL or less, for example, 10 ng/mL or less, or 5 ng/mL or less, such as 1 ng/mL or less, or 0.1 ng/mL or less, or 0.01 ng/mL or less, including 1 pg/mL or less. In certain embodiments, the system has a dynamic range from $10^{-18}$ M to 10 M, such as from $10^{-15}$ M to $10^{-3}$ M, including from $10^{-12}$ M to $10^{-6}$ M.

In certain embodiments, the microfluidic devices are operated at a temperature ranging from 1° C. to 100° C., such as from 5° C. to 75° C., including from 10° C. to 50° C., or from 20° C. to 40° C. In some instances, the microfluidic devices are operated at a temperature ranging from 35° C. to 40° C.

Utility

The subject devices, systems and methods find use in a variety of different applications where determination of the presence or absence, and/or quantification of one or more analytes in a sample is desired. For example, the subject devices, systems and methods find use in the separation and detection of proteins, peptides, nucleic acids, and the like. In some cases, the subject devices, systems and methods find use in the separation and detection of proteins. In certain instances, the proteins are native proteins (e.g., non-denatured proteins). In some cases, the microfluidic devices include a separation medium configured to separate proteins in their denatured state, and include a renaturation component configured to renature the separated proteins. The devices may be configured to separate, renature and detect proteins in a sample while substantially retaining protein activity.

In certain embodiments, the subject devices, systems and methods find use in the detection of nucleic acids, proteins, carbohydrates (e.g., glycosylated proteins or aberrantly glycosylated proteins), or other biomolecules in a sample. The methods may include the detection of a biomarker or a set of biomarkers, e.g., two or more distinct protein biomarkers, in a sample. For example, the methods may be used in the rapid, clinical detection of two or more disease biomarkers in a biological sample, e.g., as may be employed in the diagnosis of a disease condition in a subject, or in the ongoing management or treatment of a disease condition in a subject, etc. In addition, the subject devices, systems and methods may find use in protocols for the detection of an analyte in a sample, such as, but not limited to, Western blotting, Southern blotting, Northern blotting, Eastern blotting, Far-Western blotting, Southwestern blotting, and the like.

In certain embodiments, the subject devices, systems and methods find use in detecting analytes in a sample, where the analytes are biomarkers. In some cases, the subject devices, systems and methods may be used to detect the presence or absence of particular biomarkers, as well as an increase or decrease in the concentration of particular biomarkers in blood, plasma, serum, or other bodily fluids or excretions, such as but not limited to urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue, and the like. For example, the subject devices, systems and methods may be used to detect the presence or absence of a biomarker, such as, but not limited to, the aberrant glycosylation of a protein.

The presence or absence of a biomarker or significant changes in the concentration of a biomarker can be used to diagnose disease risk, presence of disease in an individual, or to tailor treatments for the disease in an individual. For example, the presence of a particular biomarker or panel of biomarkers may influence the choices of drug treatment or administration regimes given to an individual. In evaluating potential drug therapies, a biomarker may be used as a surrogate for a natural endpoint such as survival or irreversible morbidity. If a treatment alters the biomarker, which has a direct connection to improved health, the biomarker can serve as a surrogate endpoint for evaluating the clinical benefit of a particular treatment or administration regime. Thus, personalized diagnosis and treatment based on the particular biomarkers or panel of biomarkers detected in an individual are facilitated by the subject devices, systems and methods. Furthermore, the early detection of biomarkers associated with diseases is facilitated by the high sensitivity of the subject devices and systems, as described above. Due to the capability of detecting multiple biomarkers on a single chip, combined with sensitivity, scalability, and ease of use, the presently disclosed microfluidic devices, systems and methods find use in portable and point-of-care or near-patient molecular diagnostics.

In certain embodiments, the subject devices, systems and methods find use in detecting biomarkers for a disease or disease state. In certain instances, the subject devices, systems and methods find use in detecting biomarkers for the characterization of cell signaling pathways and intracellular communication for drug discovery and vaccine development. For example, the subject devices, systems and methods may be used to detect and/or quantify the amount of biomarkers in diseased, healthy or benign samples. In certain embodiments, the subject devices, systems and methods find use in detecting biomarkers for an infectious disease or disease state. In some cases, the biomarkers can be molecular biomarkers, such as but not limited to proteins, nucleic acids, carbohydrates, small molecules, and the like.

The subject devices, systems and methods find use in diagnostic assays, such as, but not limited to, the following: detecting and/or quantifying biomarkers, as described above; screening assays, where samples are tested at regular intervals for asymptomatic subjects; prognostic assays, where the presence and or quantity of a biomarker is used to predict a likely disease course; stratification assays, where a subject's response to different drug treatments can be predicted; efficacy assays, where the efficacy of a drug treatment is monitored; and the like.

The subject devices, systems and methods also find use in validation assays. For example, validation assays may be used to validate or confirm that a potential disease biomarker is a reliable indicator of the presence or absence of a disease across a variety of individuals. The short assay times for the subject devices, systems and methods may facilitate an increase in the throughput for screening a plurality of samples in a minimum amount of time.

In some instances, the subject devices, systems and methods can be used without requiring a laboratory setting for implementation. In comparison to the equivalent analytic research laboratory equipment, the subject devices and systems provide comparable analytic sensitivity in a portable, hand-held system. In some cases, the mass and operating cost are less than the typical stationary laboratory equipment. The subject systems and devices may be integrated into a single apparatus, such that all the steps of the assay, including separation, transfer, labeling and detecting of an analyte of interest, may be performed by a single apparatus. For example, in some instances, there are no separate apparatuses for separation, transfer, labeling and detecting of an analyte of interest. In addition, the subject systems and devices can be utilized in a home setting for over-the-counter home testing by a person without medical training to detect one or more analytes in samples. The subject systems and devices may also be utilized in a clinical setting, e.g., at the bedside, for rapid diagnosis or in a setting where stationary research laboratory equipment is not provided due to cost or other reasons.

Kits

Aspects of the present disclosure additionally include kits that have a microfluidic device as described in detail herein. The kits may further include a buffer. For instance, the kit may include a buffer, such as an electrophoresis buffer, a sample buffer, and the like. In certain cases, the buffer includes, but is not limited to, a Tris-glycine buffer, a tricine-arginine buffer, and the like. In some instances, the buffer includes a detergent (such as SDS or CTAB), which is employed in the electrophoretic separation of proteins, as described herein. In some instances, the kit includes a labeled binding member, such as a fluorescently labeled binding member, as described above.

The kits may further include additional reagents, such as but not limited to, release reagents, denaturing reagents, refolding reagents, detergents, detectable labels (e.g., fluorescent labels, colorimetric labels, chemiluminescent labels, multicolor reagents, enzyme-linked reagents, detection reagents (e.g., avidin-streptavidin associated detection reagents), radiolabels, gold particles, magnetic labels, etc.), calibration standards, and the like.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., diskette, CD, DVD, Blu-Ray, computer-readable memory, etc., on which the information has been recorded or stored. Yet another means that may be present is a website address which may be used via the Internet to access the information at a removed site. Any convenient means may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by mass, molecular mass is mass average molecular mass, temperature is in degrees Celsius, and pressure is at or near atmospheric.

EXAMPLES

Example 1

I. Introduction

Experiments were performed using a fully automated microfluidic device with integrated protein sizing (SDS-PAGE), protein renaturation and antibody blotting. Microfluidic devices configured for post-sizing renaturation may facilitate the reactivation of protein activity (e.g., binding affinity of proteins) after SDS-PAGE and allow for a fully integrated microfluidic Western blotting assay. Regional photopatterning of micron-scale polyacrylamide gels within a 1-mm$^2$ microfluidic chamber was used to produce discrete regions for SDS-PAGE, renaturation, transfer and immunoblotting in a single contiguous gel. Electric field generators applied electric fields in three dimensions to drive the separation and sample transfer. A renaturation component that includes a gel membrane was used to remove SDS from the separated proteins. Assay performance was tested through quantitative assessment of renaturation for green fluorescent protein (GFP).

Embodiments described herein achieve one or more of: 1) dilution and removal of SDS molecules from the proteins for renaturation, which restores proteins back to their native affinity states for subsequent immunoprobing; 2) preservation of the protein separation resolution from the first separation dimension (e.g., SDS-PAGE, protein sizing) during renaturation; 3) incorporation of post-sizing renaturation with in situ immunoblotting for fully automated microfluidic Western blotting.

II. Automated Microfluidic Western Blotting Device and Method

Experiments were performed using an integrated microfluidic based Western blotting platform, which included sample loading, SDS-PAGE, followed by membrane assisted post-sizing renaturation, sample transfer and, finally, affinity blotting. Each functional region was defined by localized photo-patterning of polyacylamide gel, as indicated in FIGS. 1(a) and 1(b). The microfluidic device allowed the steps for Western blotting (including SDS-PAGE separation, renaturation and affinity blotting) to be performed automatically on a single chip. The renaturation component included a sub-nanopore size gel membrane to filter off SDS molecules from proteins.

FIGS. 1(a) and 1(b) show images and schematics of a microfluidic Western blotting device with in-situ protein renaturation, according to embodiments of the present disclosure. FIG. 1(a) shows a bright-field image of a microfluidic Western blotting device. FIG. 1(b) shows a magnified image of the microfluidic device (FIG. 1(b), center), showing the photopolymerized loading medium 110, separation medium 120, renaturation component 130 and binding medium 140. The loading medium included a large pore-size 3% T, 3.3% C gel adjacent to a smaller pore-size (6% T) stacking gel. Renaturation components (e.g., membranes) in each side channel were 45% T, 5% C sub-nanopore size gel, only allowing SDS to pass through for SDS removal. The binding medium (e.g., blotting gel region) included a gel membrane array (6% T, 3.3% C) in the side channels that was similar in pore-size to the separation gel (6% T, 3.3% C), but included streptavidin, which allowed functionalization with biotinylated binding members (e.g., blotting reagents, such as antibodies or lectins) for target protein binding.

In the operation of microfluidic Western blotting, proteins were first electrokinetically separated in the vertical dimension. Next, the proteins were laterally transferred to the renaturation membranes which were contained in the left side array of microchannels. The protein renaturation was conducted based on the dilution and electrically stripping off of SDS molecules from proteins (see FIG. 1(b), left panel and FIG. 2(c)). After removal of SDS, the retained proteins on the membrane interfaces were laterally transferred to the binding medium which was localized in the right side array of microchannels. Antibodies or lectins were immobilized in the binding medium through streptavidin-biotin linkage and provided affinity capture for target proteins.

FIG. 2(a) shows a schematic of a microfluidic device for multi-dimensional operation, including an injector for sample loading 25, rectangular chamber for separation 21, left side microchannels for renaturation 23, and right side microchannels for binding (e.g., blotting) 24. The numbers 1-8 indicate the ports for sample injection and electrodes. FIG. 2(b) shows an image overlaid with a schematic of SDS-PAGE separation and sizing of a protein sample in a first vertical flow path. FIG. 2(c) shows an image overlaid with a schematic of the transfer of separated proteins to the renaturation membrane for renaturation in a second lateral flow path. FIG. 2(d) shows an image overlaid with a schematic of binding of target protein after renaturation by transferring to the binding medium, which was positioned in the right side channels.

The assay was automated by voltage programming, and no pressure driven flow or fluid valving was required. Incorporation of membrane assisted renaturation facilitated the integration of separation, renaturation and affinity blotting with a minimization in dead volume. The sub-nanoporous structure of the renaturation membrane allowed small SDS molecules and buffer ions to pass through, and retained larger proteins. Thus, detergent was separated from proteins which allowed the proteins to refold in native buffer. The photopatterning technique enabled parallel fabrication of renaturation membrane arrays in one step (see FIG. 3). In some instances, the microscale geometry provided enhanced mass transfer, which may facilitate rapid renaturation of proteins. A plurality of renaturation gel membranes was used to create a renaturation compartment in each side channel for individual protein pseudo-immobilization and SDS removal with buffer exchange. Thus, the renaturation of several proteins was processed simultaneously, which increased the throughput capacity of the microfluidic device.

Figure 3:
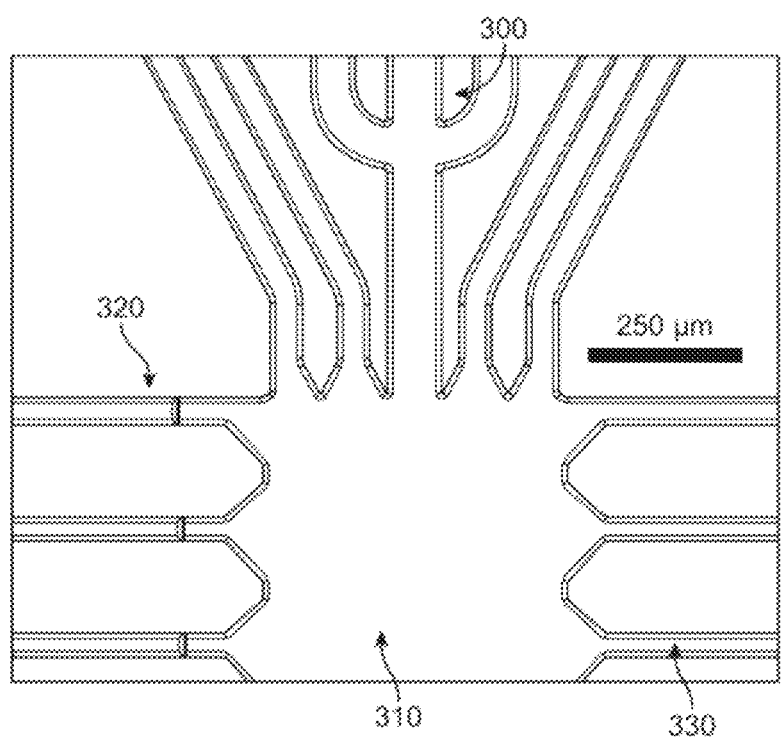
FIG. 3 shows a bright-field image of a microfluidic device, according to embodiments of the present disclosure.

FIG. 3 shows a bright-field image of a microfluidic device, according to embodiments of the present disclosure. The four different media included in the device were made by photopatterning a loading medium 300 (3% T), separation medium 310 (6% T), renaturation component 320 (45% T), and binding medium 330 (6% T, Ab) for microfluidic Western blotting.

Figure 4:
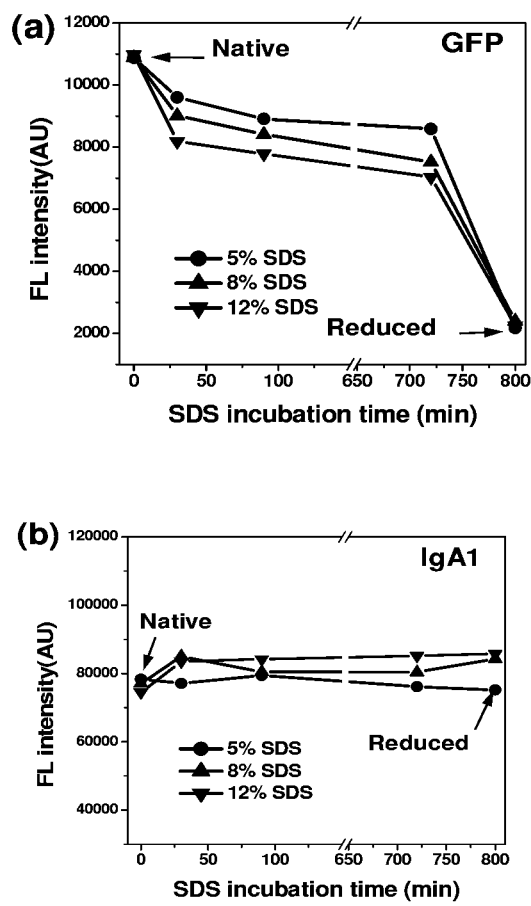
FIG. 4 shows graphs of the fluorescent emission properties of green fluorescent protein (GFP) (FIG. 4(a)) and IgA (FIG. 4(b)) treated with different concentrations of SDS and incubation times (e.g., under different denaturation conditions), according to embodiments of the present disclosure.

The renaturation performance of each side channel compartment was characterized by quantitatively assessing the renaturation of green fluorescent protein (GFP). By monitoring the fluorescent intensity of GFP, the renaturation kinetics and state were evaluated. FIG. 4 shows graphs of the fluorescent emission properties of GFP (FIG. 4(a)) and IgA (FIG. 4(b)) treated with different concentrations of SDS and incubation times (e.g., under different denaturation conditions). The reduced condition was in 2% SDS and 1% reducing agent buffer under 65° C. heating for 5 min. As shown in FIG. 4, the fluorescence of GFP was related to its native state. SDS treated GFP showed decreased fluorescent emission, due to chromophore destruction by SDS denaturation (FIG. 4(a)). The denaturation of GFP was reversible, indicated by the return of visible fluorescence.

Figure 5:
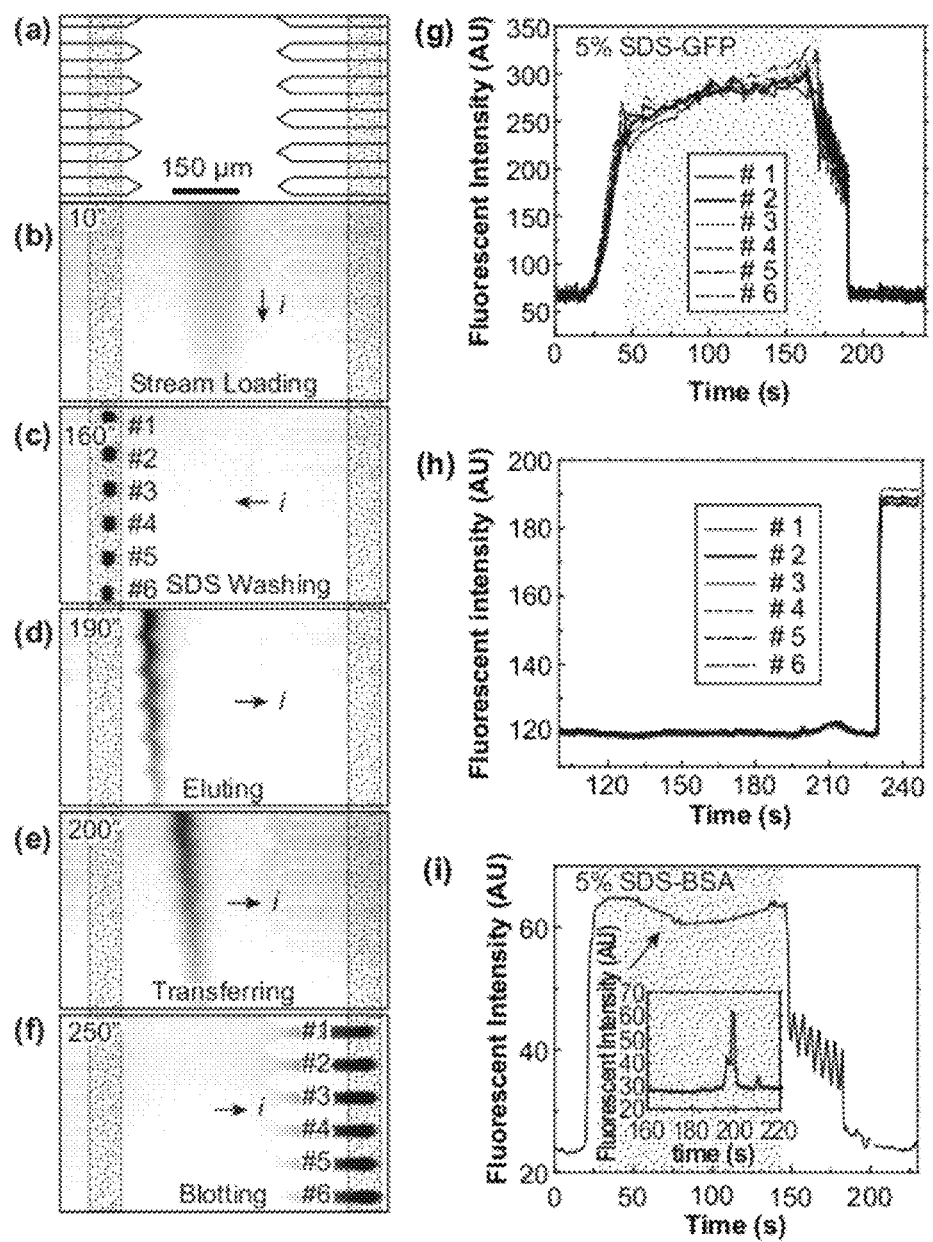
FIG. 5 shows the performance of a renaturation component and binding medium in a microfluidic Western blotting device, according to embodiments of the present disclosure.

The renaturation performance of each membrane was characterized by monitoring the GFP renaturation kinetics. As seen in FIG. 5(a), the interfaces of photopatterned membranes were located in the left side array of channels. A continuous stream of 5% SDS treated GFP was loaded into the device chamber and transferred to the left side array of channels (channels #1 to #6). GFP proteins were evenly fractionated into each renaturation compartment (FIGS. 5(b) and 5(c)). The small SDS molecules passed through the membrane and washed away under the electrokinetic flow of renaturation buffer, while the protein molecules were retained at the membrane interfaces due to size exclusion by the renaturation membrane. Increased fluorescence emission was observed at the renaturation membrane interfaces, which indicated GFP renaturation. As shown in FIG. 5(g), by monitoring the six channels in one image frame, the fluorescent intensity of GFP at the renaturation membrane increased over time. The renaturation kinetic profiles of GFP in each membrane compartment 1-6 were consistent, which indicated the reproducible performance of membrane-assisted renaturation in a high throughput manner. After renaturation, GFP proteins were eluted from the membrane interfaces, and transferred laterally to the binding medium in the right side array of channels (see FIGS. 5(d) and 5(e)). The affinity of GFP to poly anti-GFP immobilized in the binding medium was shown by the specific capture of GFP (see FIG. 5(f)). The affinity capture profile is shown in FIG. 5(h). A substantially 100% capture efficiency was achieved for each binding medium (e.g., blotting gel) and the blotting performance in each side channel 1-6 was consistent. Renaturation followed by in-situ blotting was further evaluated by introducing 5% SDS treated BSA as a negative control. As seen in FIG. 5(i), the renaturation profile of a negative control, BSA treated with 5% SDS, was significantly different as compared to GFP, due to the non-correlation of labeled fluorescence of BSA to its native state. The inset in FIG. 5(i) showed a negative response to the binding medium containing anti-GFP antibodies and there was substantially no non-specific binding of BSA to the binding medium. The time for microfluidic renaturation of 5% SDS treated GFP was about 95 s. No residual protein residues were observed on the renaturation membrane interfaces after transfer to the binding medium.

Figure 6:
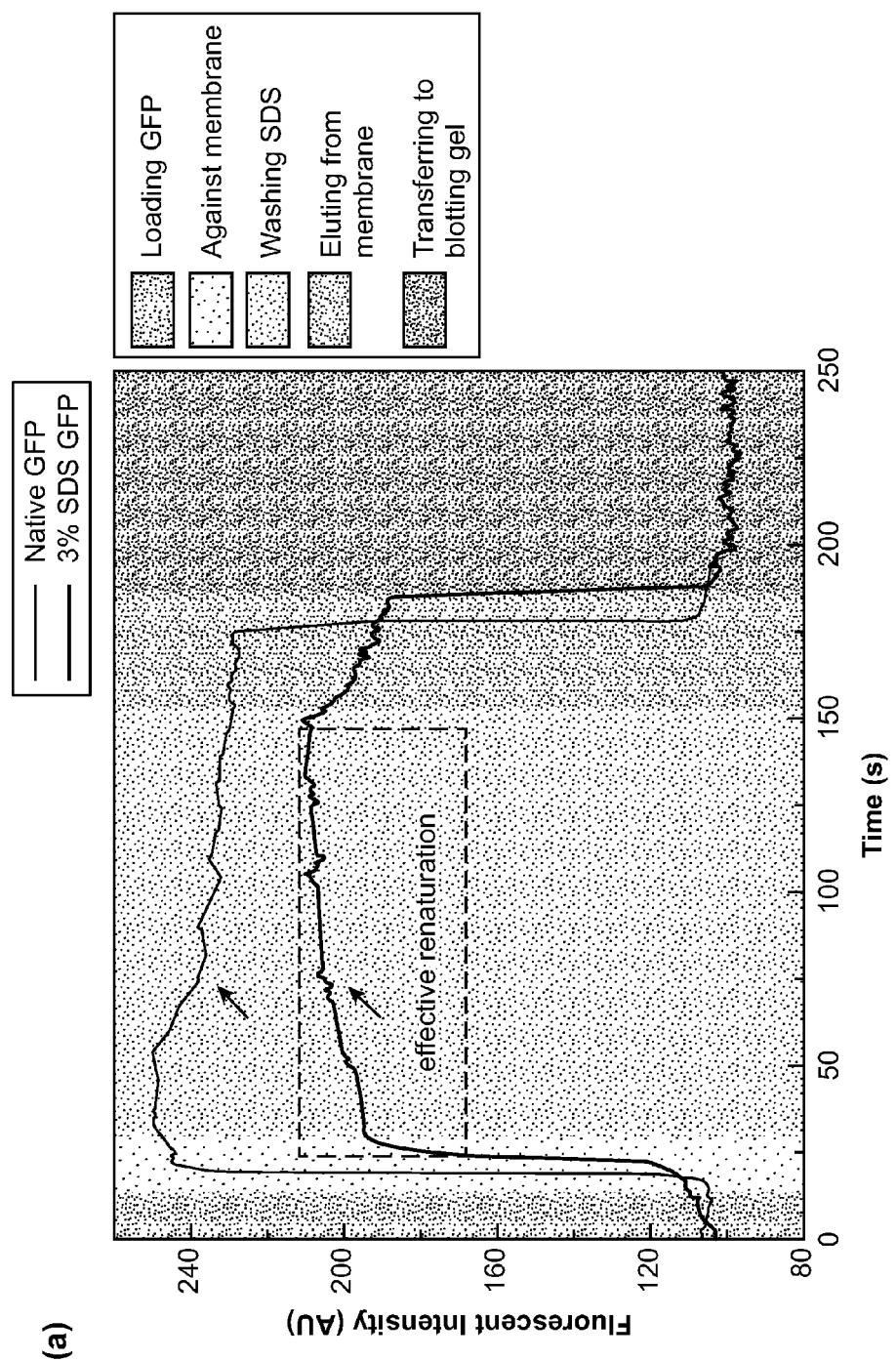
FIG. 6(a) shows a graph of the renaturation progression profile of 3% SDS treated GFP, compared with native GFP, according to embodiments of the present disclosure. Increased fluorescence for SDS treated GFP indicated effective renaturation (highlighted in the dashed line box).
FIG. 6(b) shows a graph of the kinetics of renaturation for GFP in a microfluidic device, according to embodiments of the present disclosure.
FIG. 6(c) shows a graph of the effective renaturation time, which was obtained by observing the SDS-concentration dependant fluorescence recovery, according to embodiments of the present disclosure.

The renaturation kinetic profile of GFP is shown in FIG. 6(a). FIG. 6(a) shows a graph of the renaturation progression profile of 3% SDS treated GFP, compared with native GFP. After sample loading, and lateral transfer to the renaturation membrane, 5% SDS treated GFP proteins emitted more fluorescence over time, as GFP refolded in native buffer after removal of SDS. The renaturation profile was significantly different compared to native GFP, which does not undergo the refolding process, in the same operation conditions. The kinetics of GFP for effective renaturation are shown in FIG. 6(b). FIG. 6(b) shows a graph of the kinetics of renaturation for GFP in a microfluidic device. The refolding progress curve was fit to a single exponential function with a rate constant of $k_1=2.65\times10^{-2}$ (see equation 1).

$$<(Q(t)>=A_0-A_1\exp(-k_1 t) \quad (1)$$

where $<Q(t)>$ is the value of the GFP structural property as a function of time t, and $A_0$, $A_1$, and $k_1$ are free parameters in the fitting, corresponding to the relative amplitudes and the rate constant of the refolding, respectively.

During the SDS removal step, the effective renaturation of GFP was defined according to the effectively reversed fluorescent intensity, which can be used to calculate the renaturation recovery (recovered fluorescence) by normalizing to the fluorescence of GFP in the native state (see FIG. 6(c)). FIG. 6(c) shows a graph of the effective renaturation time, which was obtained by observing the SDS-concentration dependant fluorescence recovery. The required time for GFP renaturation was proportionally responsive to the SDS concentration. For 3% SDS treated GFP, renaturation was performed in 66 s with 91% renaturation recovery.

In SDS-PAGE, the addition of SDS to the electrophoresis and sample buffer uniformly coated the proteins with negative charges, equalizing the charge for all proteins. Thus, the relative mobilities of proteins were determined solely by the sieving action of the gel, which was proportional to the molecular mass (Mr) of the proteins. Protein standards were used to establish a calibration curve for determining the molecular masses of unknown proteins.

Figure 7:
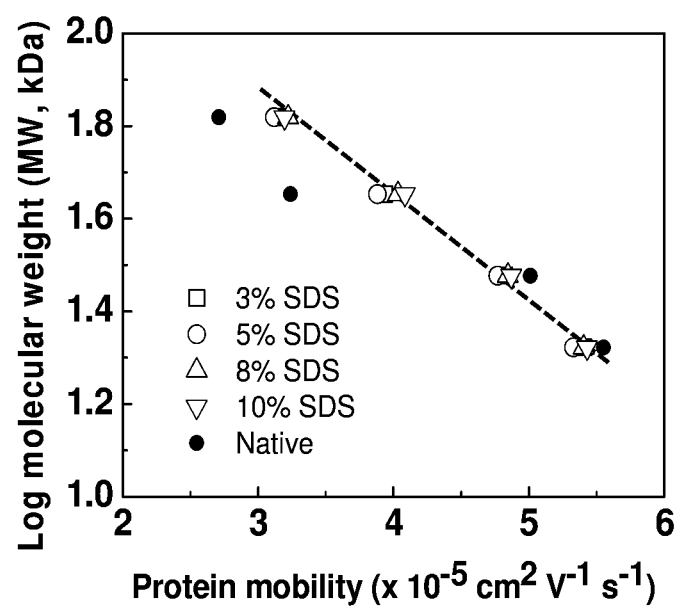
FIG. 7 shows a graph of the slab-gel SDS-PAGE calibration curve for determining protein molecular mass (Mr), according to embodiments of the present disclosure.

FIG. 7 shows a graph of a slab-gel SDS-PAGE calibration curve for determining protein molecular mass (Mr). The protein standards used were trypsin inhibitor, carbonic anhydrase, ovalbumin, and BSA. Different sample conditions, including native condition, and 3%, 5%, 8%, 10% SDS treatments, were conducted and electrophoresed in 4-12% T Tris-HCl slab gel for 2 hours. As shown in FIG. 7, the mobilities of protein standards with 3%, 5%, 8% and 10% SDS treatment were the same and showed a substantially linear relationship. In contrast, the native protein standards had a non-linear calibration curve. This indicated that 3% SDS was sufficient to coat the protein standards with negative charges and provide a substantially linear calibration curve.

Figure 8:
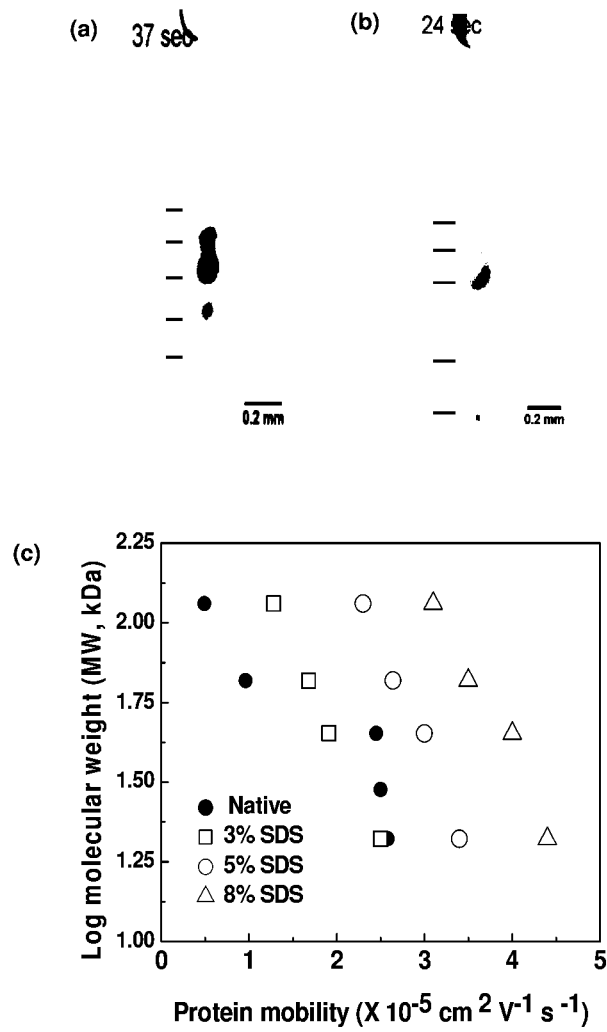
FIG. 8 shows the microfluidic device SDS-PAGE separation and molecular mass calibration curve. The protein standards used were: 1. β-galactosidase (Mr 114 kDa), 2. BSA (Mr 66 kDa), 3. Ovalbumin (Mr 45 kDa), 4. GFP (Mr 27 kDa), 5. Trypsin inhibitor (Mr 21 kDa).

The mobilities under SDS treatment were confirmed using a multidimensional microfluidic device. FIG. 8 shows a SDS-PAGE separation and molecular mass calibration curve obtained using a microfluidic device as described herein. The protein standards used were: 1. β-galactosidase (Mr 114 kDa), 2. BSA (Mr 66 kDa), 3. ovalbumin (Mr 45 kDa), 4. GFP (Mr 27 kDa), 5. trypsin inhibitor (Mr 21 kDa). FIG. 8(a) shows a fluorescence image of a native protein ladder separation using the microfluidic device. FIG. 8(b) shows a fluorescence image of an SDS-PAGE ladder separation using the microfluidic device. FIG. 8(c) shows a graph of the protein molecular mass calibration curve. Different sample conditions, including native condition, and 3%, 5%, and 8% SDS treatments, were conducted in the same multidimensional microfluidic device patterned with a 6% T separation gel (5× Tris-glycine buffer). As shown in FIG. 8, a linear relationship between protein mobility and molecular mass was obtained under 3%, 5%, and 8% SDS treatment, which was consistent with slab-gel data (see FIG. 7). This indicated that SDS treatment was effective for molecular mass calibration of unknown proteins using the microfluidic device. The native protein ladder separation showed nonlinear migration speed vs. molecular mass. Under SDS treatment, GFP had a low fluorescence emission, and was not significantly detected in the same concentration as the native (see FIGS. 8(a) and 8(b)). A shift in the slopes of the calibration curves under 3%, 5%, and 8% SDS treatments may be attributed to faster protein mobility due to covering the protein with more SDS molecules.

Figure 9:
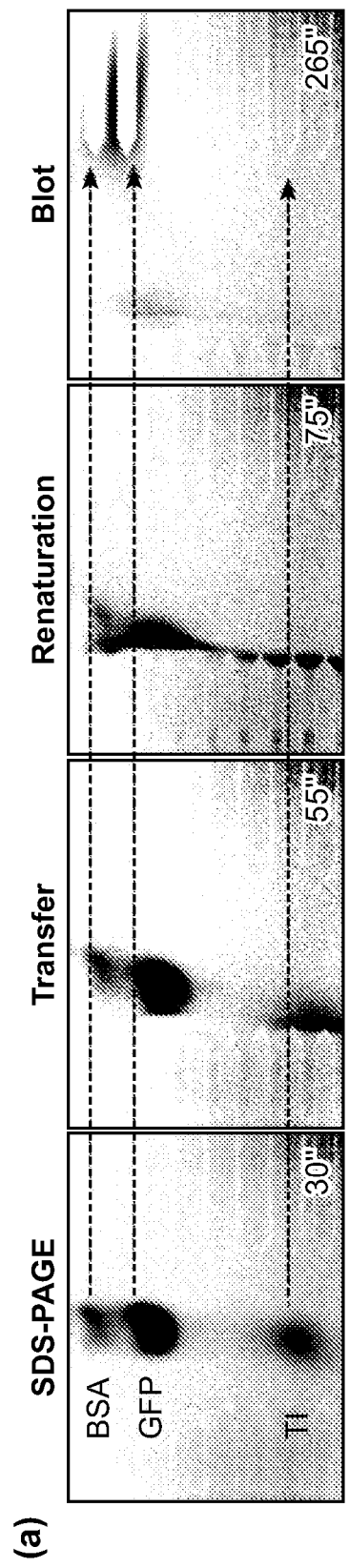
FIG. 9 shows microfluidic Western blotting of GFP with online protein renaturation, according to embodiments of the present disclosure.

Sizing information can be obtained from SDS-PAGE along the first separation flow path before transferring to the second renaturation flow path, as shown in FIG. 9. Trypsin inhibitor, GFP and BSA were separated vertically in 5% SDS in the first flow path (FIG. 9(a)). The mobilities of the three proteins were linearly related to their log molecular mass, yielding a linear calibration curve that may be used to determine the molecular mass of unknown proteins, as shown in FIG. 9(b). As shown in FIG. 9(a), the transfer step to the renaturation membrane maintained the separation resolution obtained from SDS-PAGE in the first flow path. The separated proteins were transferred into each renaturation compartment in the side channels and underwent the refolding process individually through renaturation membrane-assisted removal of SDS. The renaturation profiles for the three proteins are shown in FIG. 9(c). GFP showed an increase in fluorescence, which indicated successful refolding. After renaturation, proteins were transferred from the renaturation membrane interface towards the binding medium. An oscillated pulse voltage was used to facilitate transfer and reduce the residual protein residues retained on the membrane interface. As shown in FIG. 9(a), the proteins were completely eluted from the membrane interface and no significant sample loss was observed during the transfer steps. In the subsequent blotting step, GFP with an affinity for the binding medium was retained, while BSA and trypsin inhibitor with no affinity freely migrated past the binding medium. The target protein GFP was identified by microfluidic Western blotting in 265 s, including the 30-s SDS-PAGE separation and 100-s renaturation. Comparison of the final PAGE image to the image of proteins retained in the binding medium allowed direct spatial mapping of SDS-PAGE peak positions (molecular mass) to blotted peak positions (e.g., known antibody binding partner), and confirmed the identity of the target proteins.

Example 2

I. Introduction

Experiments were performed using a microfluidic lectin blotting platform for the identification of protein glycosylation based on protein size and affinity for specific lectins. The integrated multi-stage assay minimized manual intervention steps required for typical slab-gel lectin blotting, increased total assay throughput, reduced reagent and sample consumption, and was integrated into one device. The assay included non-reducing sodium dodecyl sulfate polyacrylamide gel electrophoresis (SDS-PAGE) followed by post-sizing SDS filtration and lectin-based affinity blotting. Renaturation components included nanoporous membranes, which retained SDS-protein complexes and allowed electrophoretic SDS removal with buffer exchange. For example, immunoglobulin A1 aberrantly glycosylated with galactose-deficient O-glycans was assayed in about 6 min using approximately 3 µL of sample.

Figure 10:
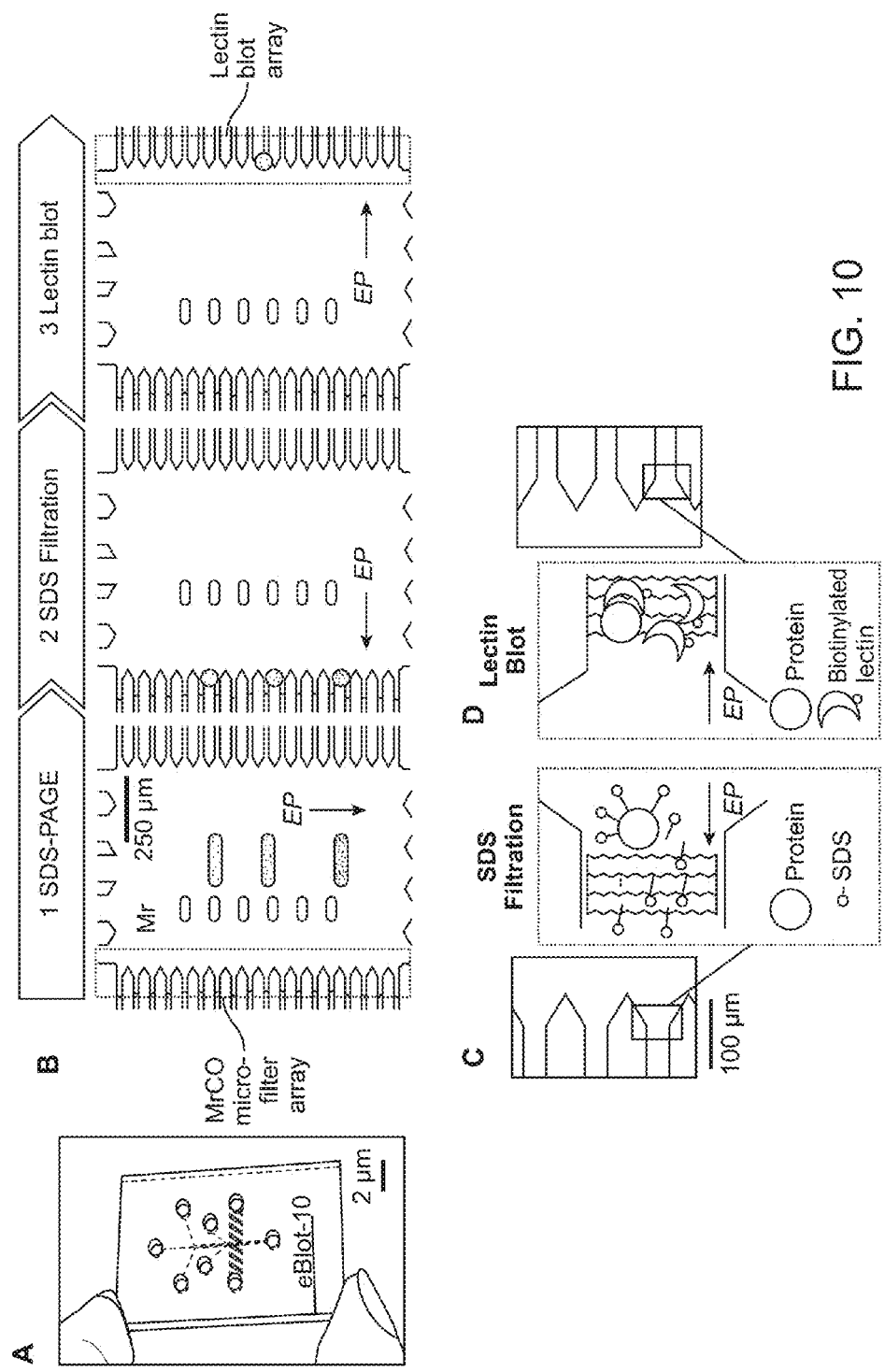
FIG. 10 shows schematics of a microfluidic device configured for protein separation, intra-assay sample manipulation, and probing with immobilized lectin, according to embodiments of the present disclosure.

Experiments were performed using an automated multidimensional microfluidic device that integrated sizing (SDS-PAGE) under non-reducing conditions with recovery of protein binding capacity by renaturation and subsequent on-chip lectin blotting (FIG. 10). The assay was performed in a glass microfluidic device housing a microchamber and microchannel network (FIG. 10A). Non-reducing SDS-PAGE retained the global glycoprotein structure and minimized non-specific (false) lectin binding that may occur under reducing conditions. A renaturation component was integrated into the microfluidic device. The renaturation component included renaturation membranes (e.g., microscale molecular mass cutoff (MrCO) filters) to dilute and remove SDS from resolved proteins after non-reducing SDS-PAGE and prior to lectin blotting (FIG. 10B). Renaturation by removing SDS from SDS-protein complexes may facilitate the recovery of protein activity (e.g., binding affinity) for previously sized proteins.

Reagents and Materials

30% acrylamide (29:1 acrylamide/bisacrylamide ratio) stock solution, 99% pure acrylamide powder and bisacrylamide powder, sodium dodecyl sulfate (SDS), and Triton X-100 were purchased from Sigma-Aldrich (St. Louis, Mo.). Premixed 10× Tris-glycine native electrophoresis buffer (25 mM Tris, pH 8.3, 192 mM glycine) was purchased from Bio-Rad (Hercules, Calif.). Premixed 10× Zymogram renaturation buffer (contained 2.5% Triton X-100) and streptavidin-acrylamide were purchased from Invitrogen (Carlsbad, Calif.). The water-soluble photoinitiator 2,2-azobis(2-methyl-N-(2-hydroxyethyl) propionamide) (VA-086) was purchased from Wako Chemicals (Richmond, Va.). Alexa Fluor 568-conjugated human serum albumin (HSA, 68 kDa), myosin heavy chain (200 kDa), β-galactosidase (114 kDa), phosphorylase B (96 kDa) were purchased from Invitrogen (Carlsbad, Calif.). Alexa Fluor 488-conjugated bovine serum albumin (BSA, 66 kDa) and trypsin inhibitor (21 kDa) were purchased from Abcam (Cambridge, Mass.). Recombinant full-length *Aequorea victoria* GFP (27 kDa) and biotinylated goat polyclonal anti-GFP were purchased from Abcam (Cambridge, Mass.). Biotinylated lectin from *Helix aspersa* (HAA) was purchased from Sigma (St. Louis, Mo.). The proteins were fluorescently labeled using Alexa Fluor 488 protein-labeling kits per the supplier's instructions (Invitrogen, Carlsbad, Calif.). Briefly, 50-100 µg antibody (~1 mg/mL) was mixed with the commercially provided reactive dye in 1M sodium bicarbonate solution (pH~8.3). The solution was incubated for 1 hour at room temperature. Every 10-15 minutes, the vial was gently inverted several times in order to mix the two reactants and increase the labeling efficiency. Extra free dye was removed by using a micro-spin column (30 kDa cut-off). Labeled proteins were stored at 4° C. in the dark until use.

IgA1 Sample Preparation

Naturally galactose-deficient IgA1 myeloma protein was isolated from plasma of a patient with multiple myeloma. Plasma was precipitated with ammonium sulfate (50% saturation). The precipitate was dissolved in and dialyzed against 10 mM sodium phosphate buffer (pH 7.0) prior to fractionation by ion-exchange chromatography on DEAE-cellulose. The purity of the IgA1 preparations was assessed by SDS-PAGE and Western blotting using an IgA-specific monoclonal antibody and IgA concentration was measured by ELISA. The molecular form of the IgA1 proteins was assessed by size-exclusion chromatography, SDS-PAGE under non-reducing conditions, and Western blots developed with anti-IgA antibody.

Pooled single-donor normal human serum (freshly collected, IPLA-CSER) was purchased from Innovative Research (Novi, Mich.). Normal human serum IgA1 was purified by using Slide-A-Lyzer dialysis (Thermo Scientific), followed with a Peptide M/Agarose column (InvivoGen).

Microfluidic Chip Fabrication

Figure 14:
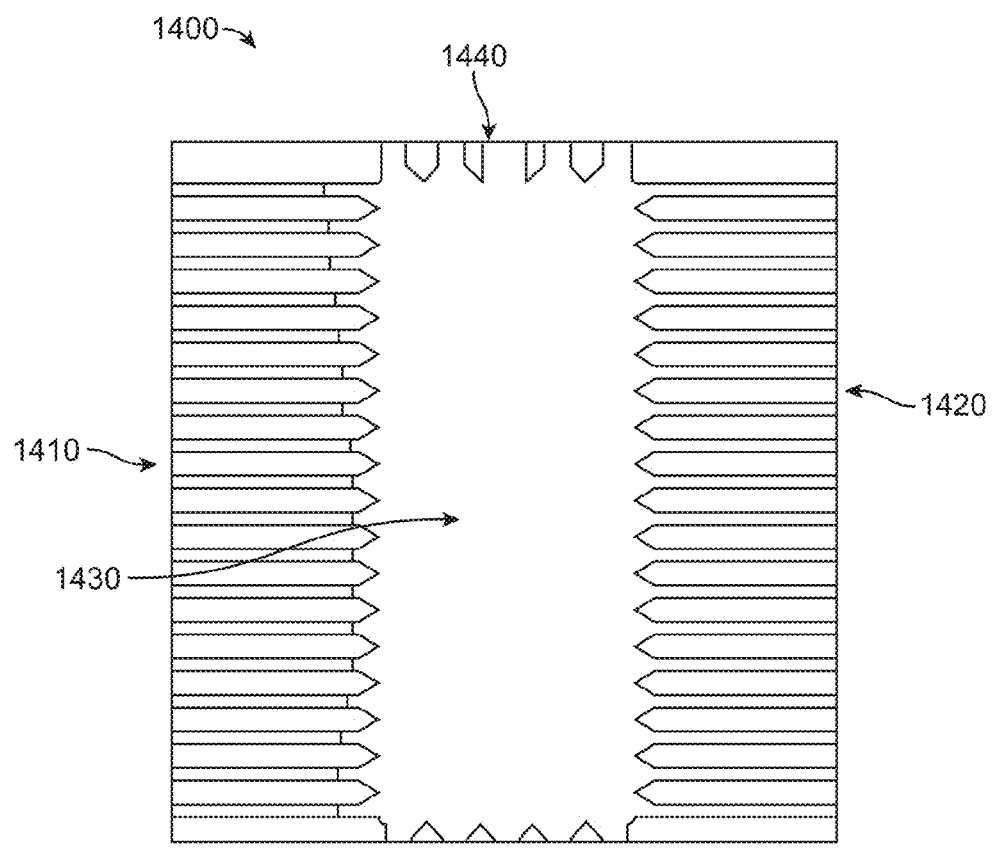
FIG. 14 shows a photograph of a microfluidic device that includes a filtration membrane, blotting gel, separation gel and loading gel, according to embodiments of the present disclosure.

Glass microfluidic chips were designed and fabricated using standard wet etch processes (see e.g., Caliper Life Sciences, Hopkinton, Mass.). Chip layouts included a cross injector and a 0.5×2 mm$^2$ rectangular microchamber connected to the reservoirs (3 µL volume each) via microchannel arrays (mask design: 20 µm deep and 10 wide; actual width: ~50 µM due to isotropic etching) on each side (FIG. 14). An array of side channels with interval spacing 100 µm, 50 µm, or 10 µm connected to the microchamber was used to form the membrane compartments for protein renaturation. The rectangular microchamber housed the separation and blotting gels. The microchannel arrays were designed to yield uniform electric fields over the microchamber in vertical and horizontal dimensions. The chip geometry was chosen to be compatible with CCD-based imaging on an epi-fluorescence microscopy system. Prior to the introduction of precursor solutions for gel fabrication, the glass chip was silanized by incubating the chip for 30 minutes with a 2:2:3:3 mixture of silane, acetic acid, methanol and water. This silanization step facilitated linking the polyacrylamide gel to the glass so that the gel would not shift under the application of an electric field.

Multifunctional Polyacrylamide Gel Photopatterning

Several functional gel regions were sequentially photopatterned within the microchamber and side channels using a four-step photolithography process. The lithography was performed using a UV objective (UPLANS-APO 4×, Olympus) in combination with a transparency film mask and epi-fluorescence microscope system (Nikon Diaphot 200, Japan). A Hamamatsu LightningCure LC5 UV light source (Hamamatsu City, Japan) with variable intensity control was used for photopatterning of the polyacrylamide gels. The UV beam from the light source was directed along the light path of the inverted epi-fluorescence microscope and up through a UV-transmission objective lens.

In Step 1, the blotting gel was fabricated by exposing a region filled with a 5% T, 3.3% C precursor solution (diluted by 1× Tris-glycine native electrophoresis buffer containing 0.4 mg/mL streptavidin-acrylamide and 1 mg/mL biotinylated lectin) to UV excitation (~12.5 mW/cm$^2$) for 330 s. The notation % T and % C indicate the percentage of total acrylamide and cross-linker, respectively. Covalently bonded streptavidin in the gel matrix was used to immobilize biotinylated antibodies or lectins for immunoblotting.

In Step 2, mask alignment to the chip was performed using a manually adjustable x-y translation stage on the microscope to subsequently photopattern an array of 500 µm wide renaturation membranes across an array of side channels. The membrane interface was determined by observing through the microscope eye piece and aligned at the junctions between the side channels and the microchamber. The composition of the renaturation membrane precursor solution was 45% T and 5% C, prepared by dilution of 99% pure acrylamide and bisacrylamide powders using 1× Tris-glycine native electrophoresis buffer. The exposure was performed at a UV intensity of ~40 mW/cm$^2$ for 85 s.

In Step 3, the PAGE separation gel was formed. The PAGE separation gel had a composition and structure similar to the blotting gel, however with no immobilized antibodies (5% T, 3.3% C, diluted by 1× Tris-glycine native electrophoresis buffer containing 0.01% TitronX-100, exposure of ~10 mW/cm² for 300 s). Titron X-100 in the separation gel was used to match the buffer strength with sample buffer in high SDS concentration.

In Step 4, a larger-pore-sized loading gel was formed using 3% T, 3.3% C acrylamide solution and an 8-min flood exposure of the chip to a filtered mercury lamp (300-380 nm, 10 mW/cm², UVP B100-AP, Upland, Calif.) with cooling fan. FIG. 14 shows a photograph of a microfluidic device 1400 that includes a filtration membrane 1410 (45% T, 5% C), blotting gel 1420 (5% T, 3.3% C, lectin), separation gel 1430 (5% T, 3.3% C), and loading gel 1440 (3% T, 3.3% C). The photopolymerization times were determined empirically based on the intensity of each UV light source, composition of acrylamide precursor solution, and desired pore-size for the desired functional region of the gel.

Each precursor solution was introduced by pressure-flushing the previous un-polymerized solution away. Each precursor contained 0.2% (w/v) VA-086 photoinitiator. Quiescent conditions were used inside the microchamber to provide a high-resolution photopatterning process and were established by applying 5% HEC drops onto each reservoir after precursor loading. A 10-min equilibration period was used before UV exposure. After use, the glass chip housings were reused through removal of the cross-linked gels. Used chips containing polyacrylamide gels were soaked in a 2:1 mixture of perchloric acid (Sigma, ACS grade, 70 wt %) and hydrogen peroxide (Sigma, ACS grade, 30 wt %) at 75° C. overnight. After gel dissolution, channels were flushed using 0.1 M sodium hydroxide for 30 min.

Apparatus and Imaging Analysis for On-Chip Assays

Image collection was performed using a CCD camera (CoolSNAP™ HQ2, Roper Scientific, Trenton, N.J.) equipped with a shutter system and an inverted epi-fluorescence microscope (IX-70, Olympus, Melville, N.Y.) with a 10× objective (UPlanFL, N.A.=0.3). Camera exposure time was 400 ms with a 10 MHz frequency. This resulted in a full-field image representing a ~1 mm×1.34-mm field of view. Use of a full-field imaging allowed all analytes to be simultaneously observed during protein separation, renaturation, transfer and final blotting in illumination shutter control. Light from a mercury arc lamp was filtered through XF100-3 or XF111-2 filter sets (Omega Optical, Brattleboro, Vt.) for illumination of AlexaFluor 488- and 568-labelled proteins, respectively. Two-color images were compiled from individual red and green wavelength image sequences taken in two separate runs on the same device. Identical conditions and timing were used for both runs. Image analysis was performed using ImageJ and regions of interest corresponding to the separation, renaturation and blotting regions were selected and consistently applied. The fluorescence profile was plotted using ImageJ across the regions of interest. The fluorescent signal was normalized to background. Separation resolution (SR) between protein bands was defined as SR=ΔL/4σ, where L was the distance between adjacent band centers and represented the average characteristic band width (Gaussian distribution fitting with OriginLab).

Electrical Control Program with Buffer Exchange

Figure 15:
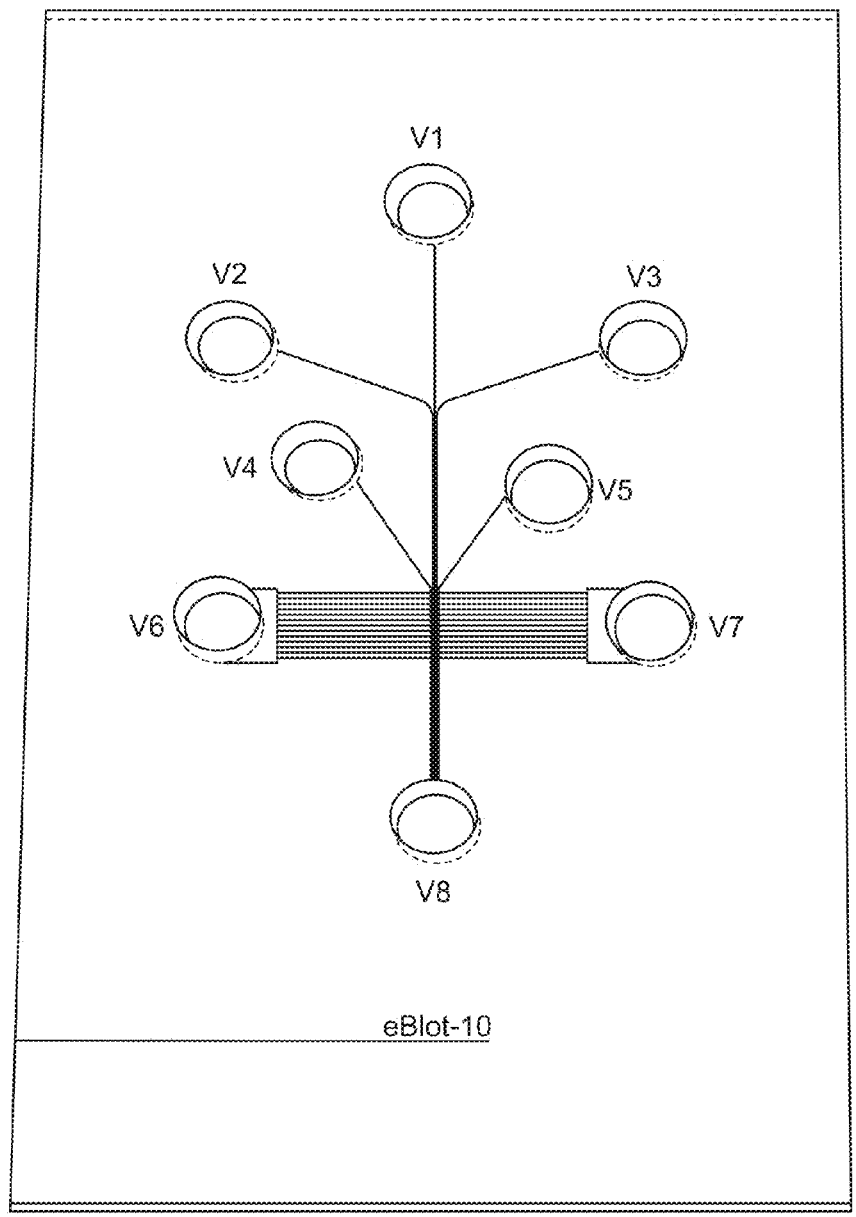
FIG. 15 shows a photograph of a microfluidic device with reservoirs labeled V1-V8, according to embodiments of the present disclosure.

After sample addition to the chip, assay operation was programmable and controlled via a power supply equipped with platinum electrodes (Caliper Life Sciences). The electric control sequences for the sample (V3), sample waste (V2), buffer (V1, V4, V5, V7), and buffer waste (V6, V8) reservoirs are indicated in Table 1, below (see also FIG. 15, which shows a photograph of the microfluidic device with reservoirs labeled V1-V8). Applied current control was used, as listed in Table 1 below.

Buffer exchange was performed during the renaturation step as indicated in Table 1. After SDS-treated proteins were transferred into individual renaturation compartments, the electric field was stopped. Each renaturation compartment physically confined the resolved protein without sample dispersion. The running buffer was replaced with renaturation buffer by pipetting ~10 μL 1× Zymogram renaturation buffer (contained 0.25% Triton X-100) into reservoirs 6 and 7. An electric field was applied again in the lateral direction for 10 s to perform the renaturation step. After renaturation, the running buffer was replaced in reservoirs 6 and 7, and the electric current control was applied again to wash away the renaturation buffer. The renaturation buffer was flushed for 50 s. The renaturation process was effective for removing SDS from proteins in concentrations up to 12% (w/v) without reducing agents. As demonstrated from both on-chip and slab-gel SDS-PAGE of standard molecular mass ladders, 3% and 5% SDS concentrations were sufficient to cover large proteins (e.g., 200 kDa) with uniform charge and produce a smooth linear correlation for molecular-mass calibration.

TABLE 1

Programmable electric control sequences over chip layout. The chip reservoirs 1 to 8 are labeled in the chip image shown in FIG. 15.

| Applied current control (μA) in each chip reservoir/Duration (s) | | V1 | V2 | V3 | V4 | V5 | V6 | V7 | V8 |
|---|---|---|---|---|---|---|---|---|---|
| ① sample loading/60 s | | −3 | 9 | −3 | 0 | 0 | 0 | 0 | −3 |
| ② separation/30-60 s | | −5 | 0.5 | 0.5 | −4 | −4 | 0 | 0 | 12 |
| ③ transfer for renaturation/10-30 s | | 0 | 0 | 0 | 0 | 0 | 2 | −2 | 0 |
| ④ renaturation | Stop electric flow for buffer exchange/20 s | 0 | 0 | 0 | 0 | 0 | 0 | 0 | 0 |
| | Flush renaturation buffer/50 s | 0 | 0 | 0 | 0 | 0 | 2 | −2 | 0 |
| | Oscillating voltage 4 s | 0 | 0 | 0 | 0 | 0 | −0.5 | 0.5 | 0 |
| | (repeat five circles)/40 s 4 s | 0 | 0 | 0 | 0 | 0 | 0.5 | −0.5 | 0 |
| ⑤ transfer to blot/30-60 s | | 0 | 0 | 0 | 0 | 0 | −2 | 2 | 0 |

Figure 16:
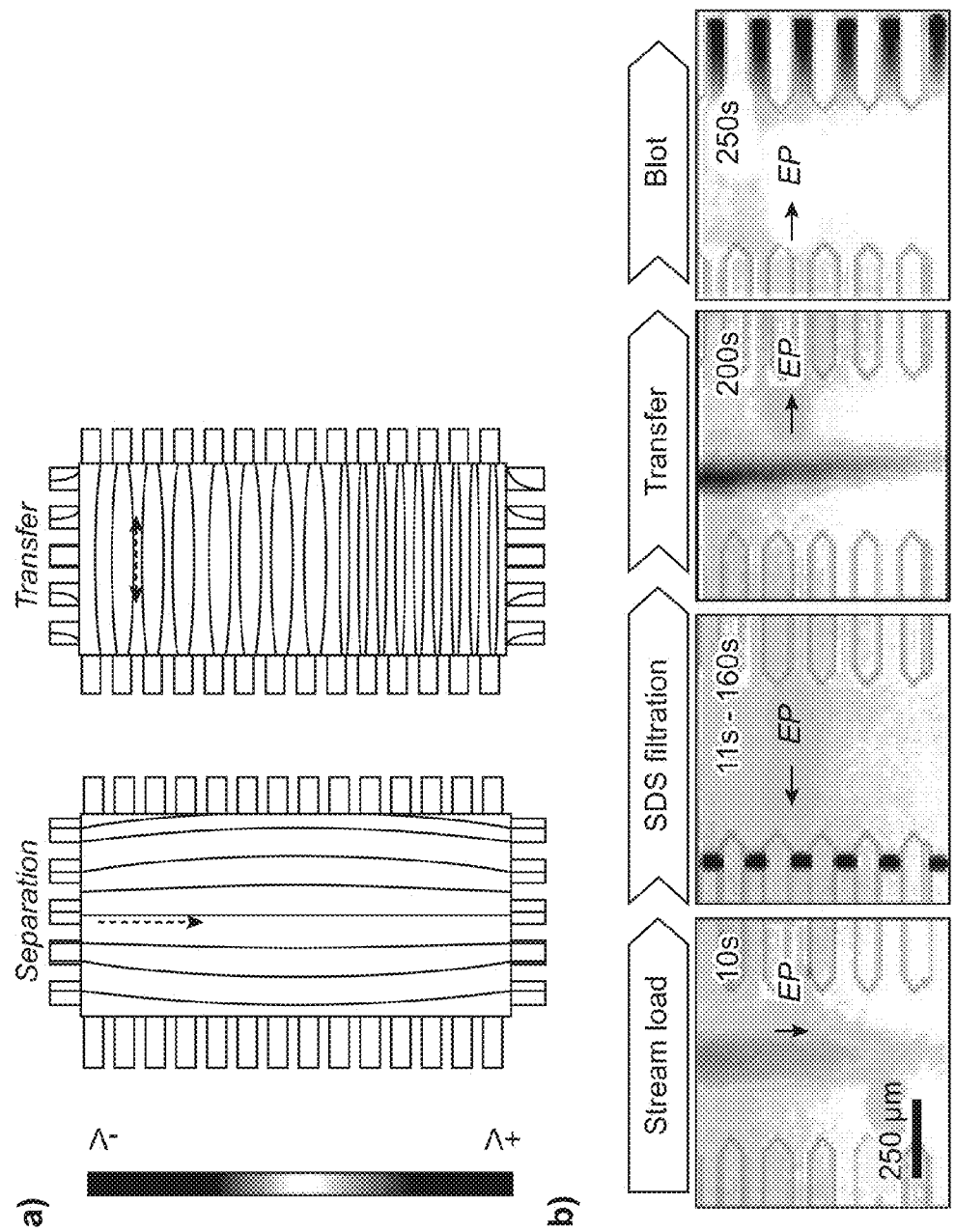
FIG. 16(a) shows schematics of a COMSOL simulation showing the electric field distribution within the chip chamber geometry during the separation and lateral transfer process, according to embodiments of the present disclosure.
FIG. 16(b) shows fluorescence micrographs illustrating the four-step renaturation of 5% SDS treated GFP in the microchamber flanked by (left) small pore-size filtration membranes and (right) antibody-laden blotting membranes, according to embodiments of the present disclosure.

The applied electric field in the vertical and horizontal dimensions within the designed geometry was simulated by using COMSOL Multiphysics (Version 4.0a, COMSOL AB), as shown in FIG. 16(a). The straight and uniform electric field distribution facilitated the precise manipulation of the sample in three directions during separation, renaturation, transfer and blotting. Both experiments and simulation showed a well-controlled electric field distribution in the vertical and horizontal dimensions within the designed geometry (FIGS. 16(a) and 16(b)). Renaturation took place after stream loading between 11 s to 160 s. In FIG. 16(b), a continuous loading of a vertical stream of GFP showed the horizontal transfer process was performed with a minimization in the dispersion of the sample. The distortion of the stream shape after crossing the separation gel twice was less than 5% (see FIG. 16(b)).

On-Chip Renaturation Kinetics

Unlike that for pre-labeled proteins, the fluorescence of GFP was related to its native state. The GFP denaturation process was reversible by showing the return of visible fluorescence. This fluorescence recovery made GFP a useful model for monitoring the renaturation kinetics of the microfluidic device. The recovery of renatured GFP was calculated by normalizing to the corresponding fluorescence of non-denatured GFP in the same conditions. A kinetic trace was obtained experimentally by plotting the restored fluorescence at a given time. The resulting graph was fit to a double-exponential function:

$$\langle Q(t) \rangle = A_0 - A_1 \exp(-k_1 t) - A_2 \exp(-k_2 t),$$

where Q(t) is the value of restored fluorescence as a function of time, and $A_0$, $A_1$, $A_2$, $k_1$, and $k_2$ are free parameters in the fitting, corresponding to the relative amplitudes and the rate constants of the phases, respectively. Using the formula above, the rate constant and half time in the kinetic mechanism were determined. The renaturation process started from transfer and continued during filtration through membrane. To avoid any enrichment-induced increase in fluorescence, the progress-curves were the depiction of fluorescence after complete transfer. The secondary rate constant (k) from renaturation kinetics was used to express the half time according to the function: Half time (t)=ln 2/k.

TABLE 2

Kinetic analysis of renaturation progress under different SDS concentration (w/v %) treatments

Figure 19A:
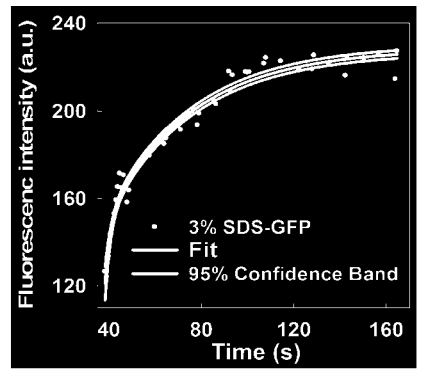
FIGS. 19(a)-19(d) show regression curves for Table 2, according to embodiments of the present disclosure.
Figure 19B:
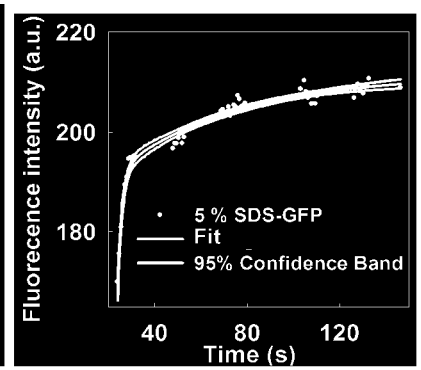
Figure 19C:
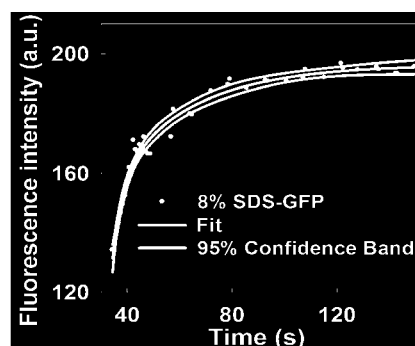
Figure 19D:
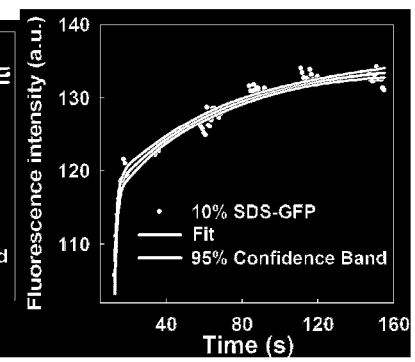

| Kinetics | 3% SDS-GFP | 5% SDS-GFP | 8% SDS-GFP | 10% SDS-GFP |
|---|---|---|---|---|
| Regression curves | See FIG. 19(a) | See FIG. 19(b) | See FIG. 19(c) | See FIG. 19(d) |
| Correlation | $R^2 = 0.97$ | $R^2 = 0.98$ | $R^2 = 0.98$ | $R^2 = 0.96$ |
| Rate constant ($s^{-1}$) | 0.0265 | 0.0189 | 0.0130 | 0.0112 |
| Half time (s) | 26.1 | 36.7 | 53.3 | 61.8 |

Nyquist-Shannon Sampling Based Protein Collection by Renaturation Compartment Array According to the Nyquist-Shannon sampling theorem, in order to reconstruct a signal without any aliasing, the sampling frequency is at least equal or greater than the maximum frequency of the signal being sampled. The sampling theorem indicates that the uniformly spaced discrete samples are a complete representation of the signal if this sampling bandwidth (here the channel space) is equal or less than the bandwidth of signal being sampled (here the protein bandwidth). Based on this theorem, the sufficient condition for exact reconstructability from samples in a uniformly spaced channel array is: Ws≤Wp. The term Ws is the channel space interval in the side channel array, and Wp is the protein band width (see FIGS. 21(a) and 21(b)).

The separation resolution is defined by the following equation:

$$SR = \frac{C_2 - C_1}{1/2 W_{C1} + 1/2 W_{C2}}$$

Figure 21A:
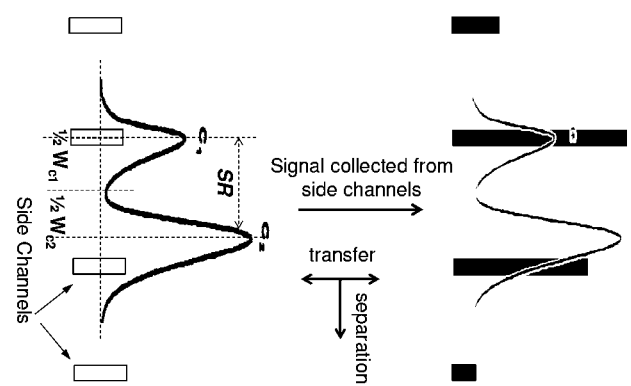
FIG. 21(a) shows a graph indicating that aliasing causes decreased separation resolution.
Figure 21B:
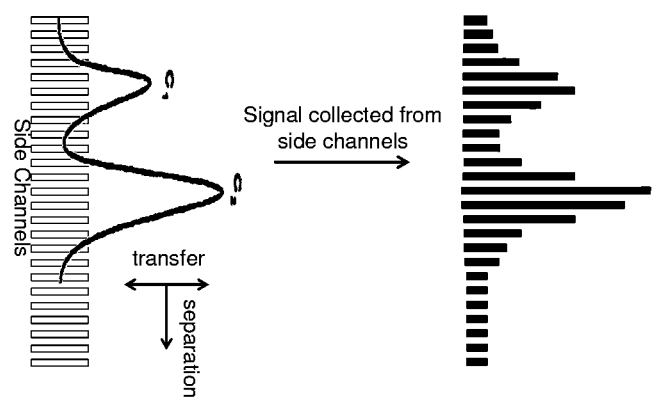
FIG. 21(b) shows a graph indicating that high density of side channels produces well reconstructed signal without aliasing, according to embodiments of the present disclosure.

A baseline separation is SR=1 (see FIG. 21(a)). For two proteins with a bandwidth of ~50 μm in baseline separation, the width between two peak centers is about 50 μm. The sufficient condition of a complete representation of the SR is that the interval of collection side-channel is equal or less than 50 μm.

TABLE 3

The variance characterized from parallel side channel sampling during the lateral transfer process.

| | Mr shifting (kDa)[a] | | SR variance (RSD %) | |
|---|---|---|---|---|
| | 50-μm spacing microchannel array | 10-μm spacing microchannel array | 50-μm spacing microchannel array | 10-μm spacing microchannel array |
| SR > 1.5 | ~2 | — | 3.1% | — |
| SR = 1~1.5 | ~8 | ~2 | 3.5% | 3.2% |
| SR < 1 | ~12 | ~5 | 9.3% | 3.3% |

[a]Mr shifting from Mr calibration was based on center peak shifting

II. Membrane-Assisted Renaturation for Microfluidic Lectin Blotting

Figure 17:
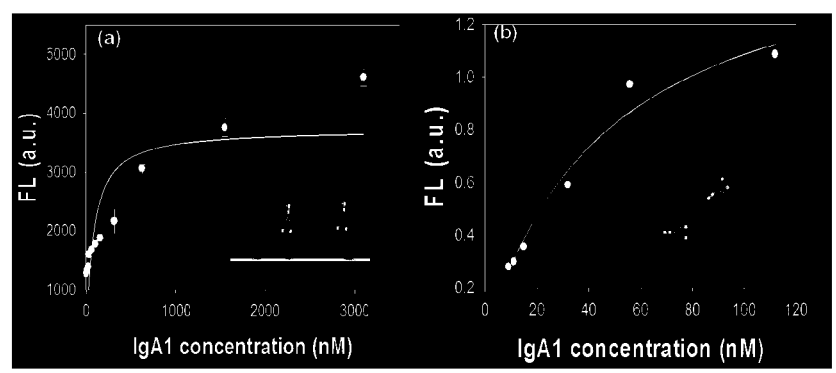
FIGS. 17(a) and 17(b) show graphs of the dissociation constant of HAA binding to galactose-deficient IgA1 as measured by ELISA (FIG. 17(a)) and on-chip lectin blotting gel (FIG. 17(b)). The $K_d$ measured by ELISA through surface immobilization was 73.1 nM (FIG. 17(a)). The $K_d$ measured through on-chip lectin blotting gel was 47.2 nM (FIG. 17(b)).

The renaturation component included renaturation membranes (e.g., MrCO microfilters) made of polyacrylamide (PA) gel membranes located in a microchannel array flanking the central microchamber. The MrCO microfilters were fabricated using one-step photopatterning of a 45% T PA gel in the channel array (FIG. 10C). As a result of their placement in channels, the filters defined compartments that allowed electrophoresis-assisted lateral buffer exchange and SDS filtration (see FIG. 10B and Table 1). The microfilters excluded transport of species with Mr>20 kDa, thus allowing buffer and SDS to exit the chamber, as indicated in the schematic inset in FIG. 10C. After SDS removal, proteins were transported to a binding medium (e.g., blotting region) flanking the opposite side of the microchamber (FIG. 10D). The PA blotting gels included streptavidin acrylamide, which was bonded to biotinylated antibody or lectin. Analytes with affinity for the immobilized species were retained. Other species were transported through the binding medium and electromigrated out of the array. In FIGS. 10B-10D, arrows labeled "EP" indicate the direction of electrophoresis. Directed electrophoresis through the three-dimensional reactive "pores" in the blotting region may facilitate mass transport by reducing the diffusion distance and facilitate an increase in binding through controlled orientation of the capture reagent (see FIG. 17(b)). The use of multidimensional electric field control in the 0.5 mm×2 mm gel-patterned microfluidic chamber allowed the separation, renaturation and blotting assay to be performed in one integrated microfluidic device in an automated format (see FIG. 16(b) and Table 1).

Figure 18:
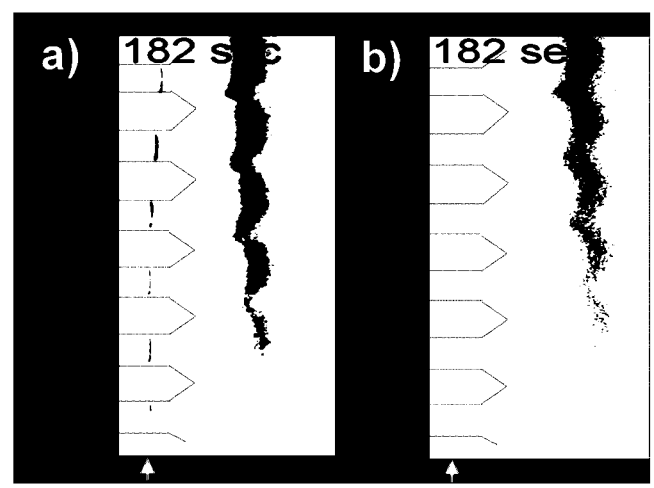
FIG. 18 shows CCD images showing the membrane interfaces after renaturation transfer for blotting, according to embodiments of the present disclosure. The arrows indicate the membrane interface positions. The protein residues observed at the membrane interfaces after lateral transfer indicated the sample loss (FIG. 18(a)). Applying oscillating voltage sequences at the end stage of renaturation minimized the post-renaturation sample loss (FIG. 18(b)).

The MrCO microfilters were configured to allow buffer ions and SDS monomers (Mr=288 kDa) to flow out of the microchamber while retaining larger species such as proteins (>20 kDa). The critical micelle concentration (CMC) of SDS is 6-8 mM (~0.23% w/v). Above the CMC, SDS micelles form with a maximum Mr of 16 kDa and break up into monomers upon dilution. Both SDS-treated trypsin inhibitor (TI, 21 kDa) and green fluorescent protein (GFP, 27 kDa) were empirically determined to be excluded from electromigration through the microfilters (see e.g., FIG. 16(b)). The electrophoretic mobility of SDS micelles was higher than that of the model proteins ($\mu_{SDS}$=-6.0×10$^{-4}$ cm$^2$ V$^{-1}$ s$^{-1}$ vs $\mu_{TI}$=-2.0×10$^{-4}$ cm$^2$ V$^{-1}$ s$^{-1}$, both at pH 7.0). Thus, SDS micelles electromigrated more quickly under the same applied electric field with other conditions held constant. As such, the SDS removal process was not a rate-limiting step for protein renaturation. During the renaturation step, an oscillating voltage was applied to minimize protein entanglement or adsorption to the MrCO PA gel (see Table 1 and FIG. 18). By applying oscillating voltage sequences at the end stage of renaturation, post-renaturation sample loss was reduced by about 16.6%.

Figure 11:
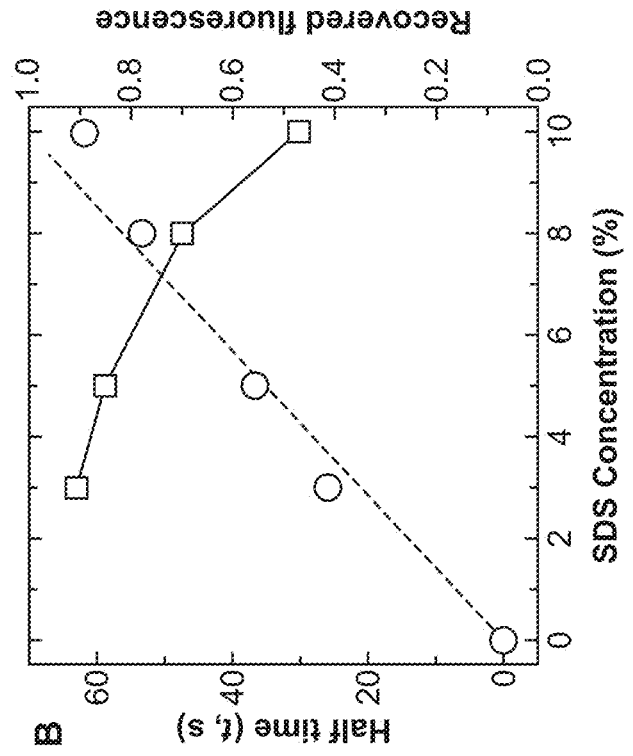
FIG. 11 shows graphs of the renaturation of 5% SDS-treated GFP during treatment at on-chip MrCO microfilters, according to embodiments of the present disclosure.
Figure 11:
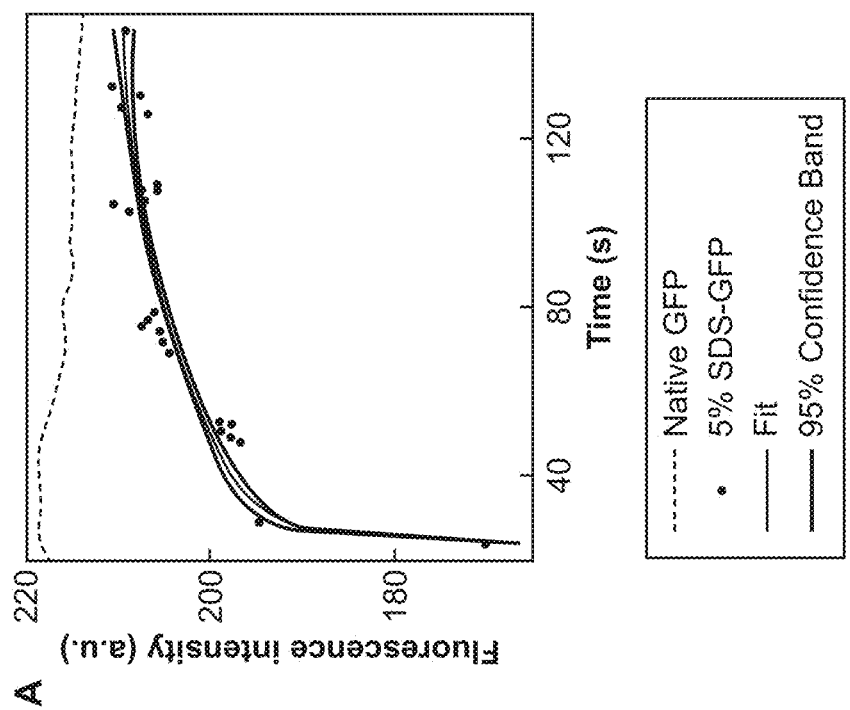
Figure 20:
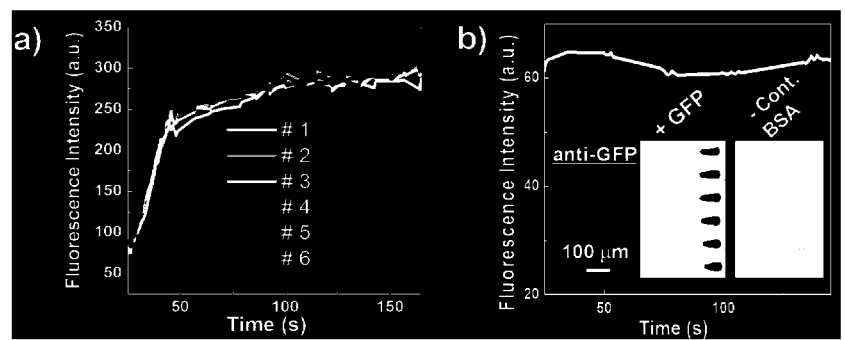
FIG. 20(a) shows a graph of the performance of the on-chip renaturation compartment array, according to embodiments of the present disclosure.
FIG. 20(b) shows a graph of on-line renaturation progress-curve from 5% SDS-BSA as a negative control, according to embodiments of the present disclosure.

Since GFP fluorescence is correlated with structure, GFP renaturation was monitored by detecting the fluorescence signal of SDS-treated GFP (SDS-GFP) at the microfilters during buffer exchange and SDS removal (recovered fluorescence). To assess the fluorescence recovery of SDS-GFP during renaturation by the MrCO microfilters, a stream of 5% SDS-GFP was electrophoresed into the microchamber and then transferred to the MrCO microfilters (see FIG. 16(b)). Fluorescence recovery for native GFP was detected and showed a gradual decrease in fluorescence signal (FIG. 11A). In contrast, 5% SDS-GFP showed a significant increase in fluorescence signal, indicating GFP renaturation. Double-exponential fits of the recovered fluorescence in handling-time courses for GFP treated with a range of SDS concentrations yielded estimates of both the renaturation rate constant (k) and half-time (t) (see FIG. 11B and Table 2). The recovered fluorescence was inversely related to the SDS concentration in the sample, indicating that less SDS in the initial sample facilitated the renaturation process. The consistent performance of GFP renaturation at the MrCO microfilter array is shown in FIG. 20. FIG. 20(a) shows a graph of the performance of the on-chip renaturation compartment array that included side channels #1-6. A stream loading of 5% SDS-GFP was distributed into each renaturation compartment #1-6. The recovered fluorescence was detected from each individual compartment in parallel, and showed consistent renaturation efficiency over all 6 channels. FIG. 20(b) shows a graph of a renaturation progress-curve from 5% SDS-BSA as a negative control. The inset shows the subsequent blotting profile after renaturation. The GFP blotting gel included anti-GFP antibodies immobilized through streptavidin-biotin linkage. BSA did not detectably bind to the GFP blotting gel.

Figure 22:
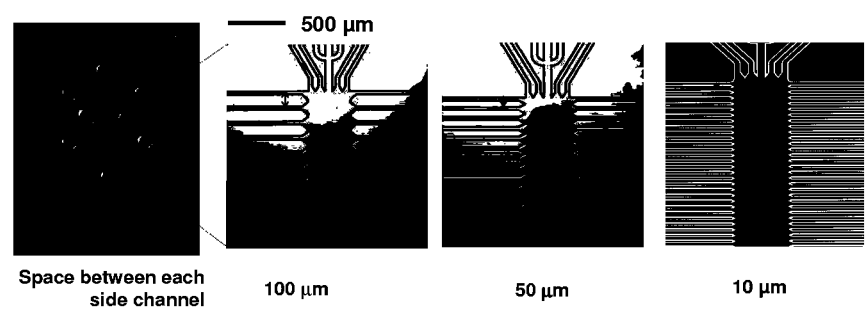
FIG. 22 shows bright field images of various array network designs in glass chips, according to embodiments of the present disclosure. Both the width of each side channel and the spacing between neighboring channels were adjusted.

Experiments were performed to determine intra-assay losses due to sample handling and integrated use of the MrCO microfilter. A microfluidic device that included a microfilter channel array was fabricated with distances (e.g., pitches) of 10 and 50 μm between the channel centerlines. Molecular mass (Mr) protein ladders were transferred from the SDS-PAGE separation axis to the lateral microchannel arrays (see FIG. 22 and Table 3).

Figure 12:
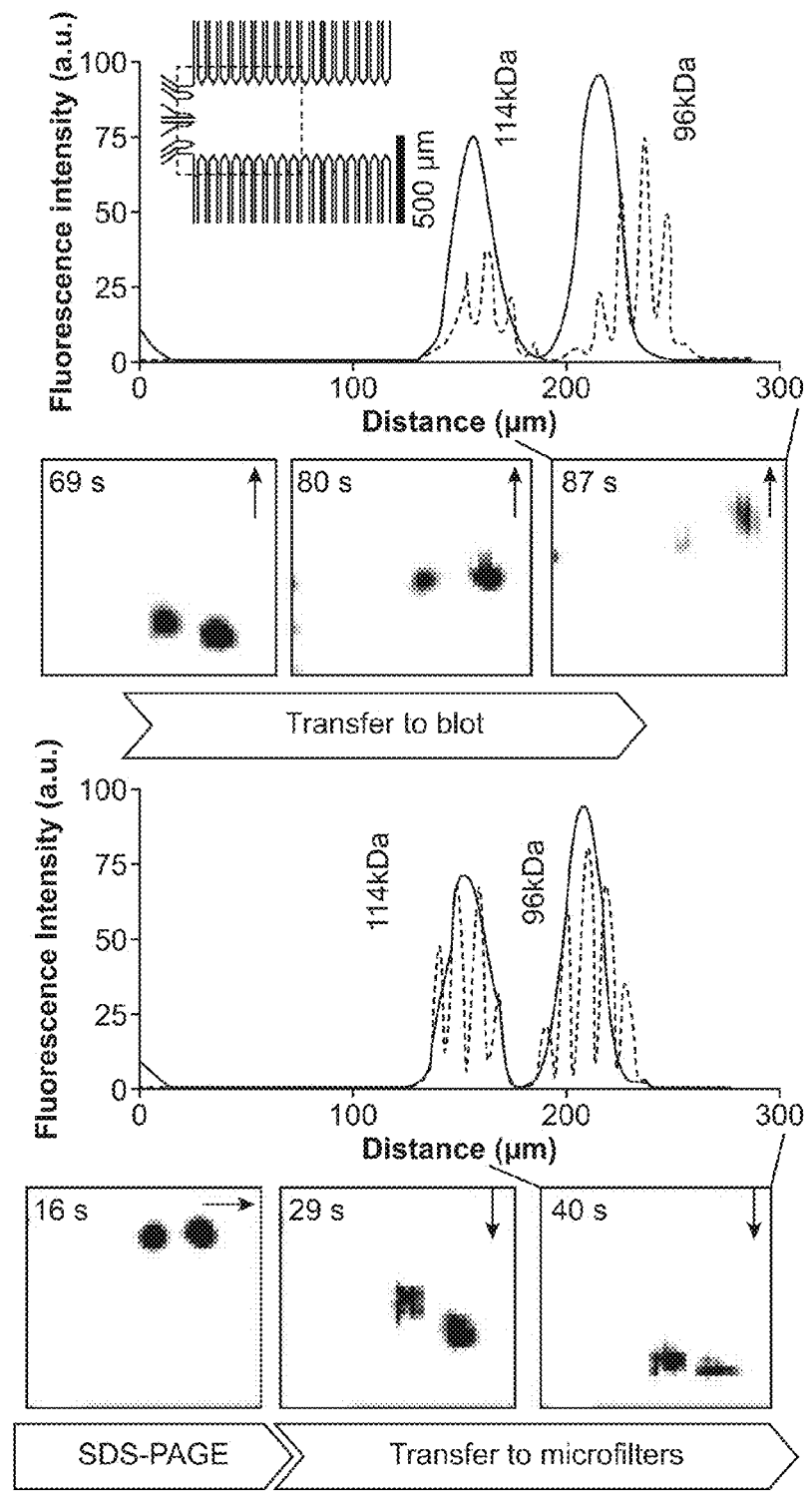
FIG. 12 shows fluorescence micrographs and graphs characterizing transfer losses arising from intra-assay sample handling and treatment, according to embodiments of the present disclosure.

FIG. 12 shows micrographs and graphs characterizing transfer losses arising from intra-assay sample handling and treatment. The fluorescence micrographs show the time evolution of the integrated assay for two model proteins (phosphorylase B (96 kDa) and β-galactosidase (114 kDa); 5% SDS treatment). Plots of the fluorescence intensity distribution on the separation axis (gray lines) were compared with the fluorescence intensity distributions in the MrCO microfilter array (dashed black line at 40 s) and the blotting array (dashed black line at 87 s). Arrows indicate the direction of electrophoresis. The array channel spacing was about 10 μm. The chip design and imaging region are shown in the inset. FIG. 12 shows that oversampling of the protein zones minimized de-separation and Mr information losses (see also FIG. 23 and Table 3). In this case, the loss of Mr information was about 5 kDa, with separation resolution (SR) losses of <4%.

Figure 23:
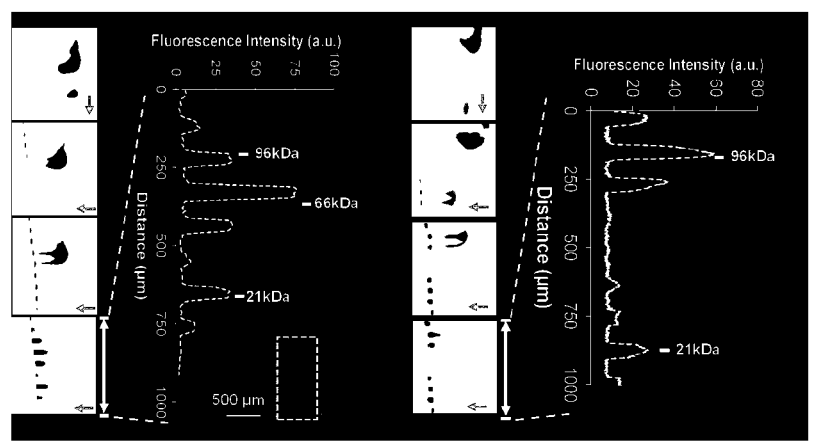
FIG. 23 shows fluorescence micrographs of the time evolution of an integrated assay for several model proteins (phosphorylase B (96 kDa), bovine serum albumin (66 kDa), and trypsin inhibitor (21 kDa); 5% SDS treatment), according to embodiments of the present disclosure.

FIG. 23 shows fluorescence micrographs of the time evolution of an integrated microfluidic assay for several model proteins (phosphorylase B (96 kDa), bovine serum albumin (66 kDa), and trypsin inhibitor (21 kDa); 5% SDS treatment). Plots of fluorescence intensity distribution on the separation axis (gray lines) were compared to fluorescence intensity distribution in both the MrCO microfilter array (dashed black line) and the blotting array (dashed black line). Arrows indicate the direction of electrophoresis. The array channel spacing was about 50 μm. The chip design and the imaging region are shown in the inset. The spaced discrete samples on the MrCO microfilter array correlated with the protein signals in the PAGE separation medium.

Figure 24A:
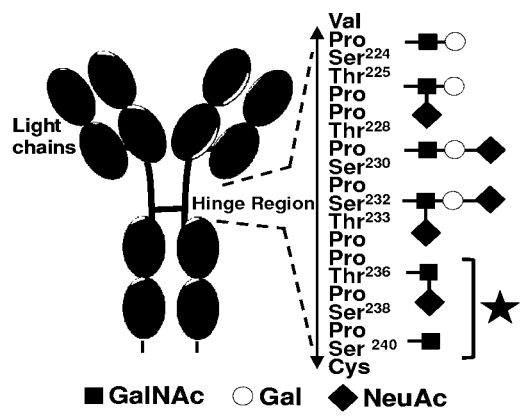
FIG. 24(a) shows a schematic of possible β-glycan structures in the hinge region of human IgA1, including aberrant glycosylation, i.e., galactose-deficient variants (two bottom structures indicated by the star). Ser/Thr residues as potential sites of β-glycan attachment are also indicated.
Figure 24B:
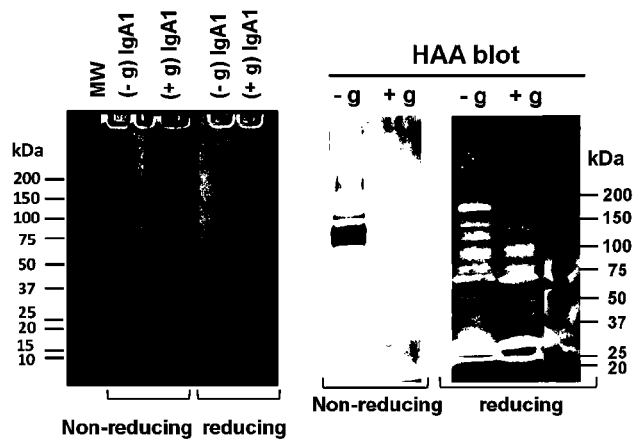
FIG. 24(b) shows fluorescence images of non-reducing SDS-PAGE of galactose-deficient IgA1 (–g) myeloma protein and IgA1 from normal human serum (+g), compared with reducing PAGE condition (FIG. 24(b), left), and HAA blotting of galactose-deficient IgA1 (–g) myeloma protein compared with normal human serum IgA1 (+g) (FIG. 24(b), right).

Experiments were performed using an integrated on-chip lectin blotting assay to assess human immunoglobulin A1 (IgA1) aberrantly glycosylated with galactose-deficient O-glycans. This IgA1 glycosylation aberrancy is typical for IgA nephropathy (IgAN). IgAN is the most common primary glomerulonephritis, frequently leading to end-stage renal disease. Specifically, O-glycans attached to serine and threonine residues in the hinge region of the a1 heavy chain in IgA1 are deficient in galactose and thus have exposed terminal N-acetyl-galactosamines (GalNAc) (FIG. 24(a)). In contrast, normal IgA1 O-glycans include GalNAc and galactose. Thus, aberrantly glycosylated serum IgA1 is a potential glycosylation-associated IgAN biomarker. FIG. 24(a) shows a schematic of possible O-glycan structures in the hinge region of human IgA1, including aberrant glycosylation, i.e., galactose-deficient variants (two bottom structures indicated by the star). Ser/Thr residues as potential sites of O-glycan attachment are also indicated. Typically, 6 sites are glycosylated. NeuAc indicates N-acetylneuraminic acid, and Gal indicates galactose. FIG. 24(b) shows fluorescence images of non-reducing SDS-PAGE of galactose-deficient IgA1 (−g) myeloma protein and IgA1 from normal human serum (+g), compared with reducing PAGE conditions (FIG. 24(b), left), and HAA blotting of galactose-deficient IgA1 (−g) myeloma protein compared with normal human serum IgA1 (+g) (FIG. 24(b), right). Helix aspersa (HAA) was specific for terminal GalNAc on galactose-deficient IgA121. A 4-12% precast polyacrylamide slab mini-gel was used with Tris-glycine buffer, pH 8.3. A weak positive response (non-specific) from normal human IgA1 under reducing condition was observed. Compared with reducing conditions that only showed H and L chains, IgA1 protein shows a 160 kDa monomer form under non-reducing condition, which would be well resolved from IgG (150 kDa).

Experiments were performed to assess lectin binding to naturally galactose-deficient IgA1 myeloma protein that mimicked the aberrancy found in IgA1 from patients with IgAN. Lectin from Helix aspersa (HAA) is specific for terminal GalNAc on galactose-deficient IgA121 and thus was immobilized in the blotting region. Normally glycosylated IgA1 purified from the serum of a healthy individual was used as a negative control (e.g., no interaction with HAA was expected). Conventional HAA lectin slab-gel blotting was performed (FIG. 24(b)), and HAA bound to the IgA1 myeloma protein, confirming that the O-glycans of IgA1 were galactose-deficient. HAA did not bind to IgA1 from normal human serum, which indicated that this IgA1 was normally glycosylated. A non-specific (false) response under reducing conditions was observed.

Figure 13:
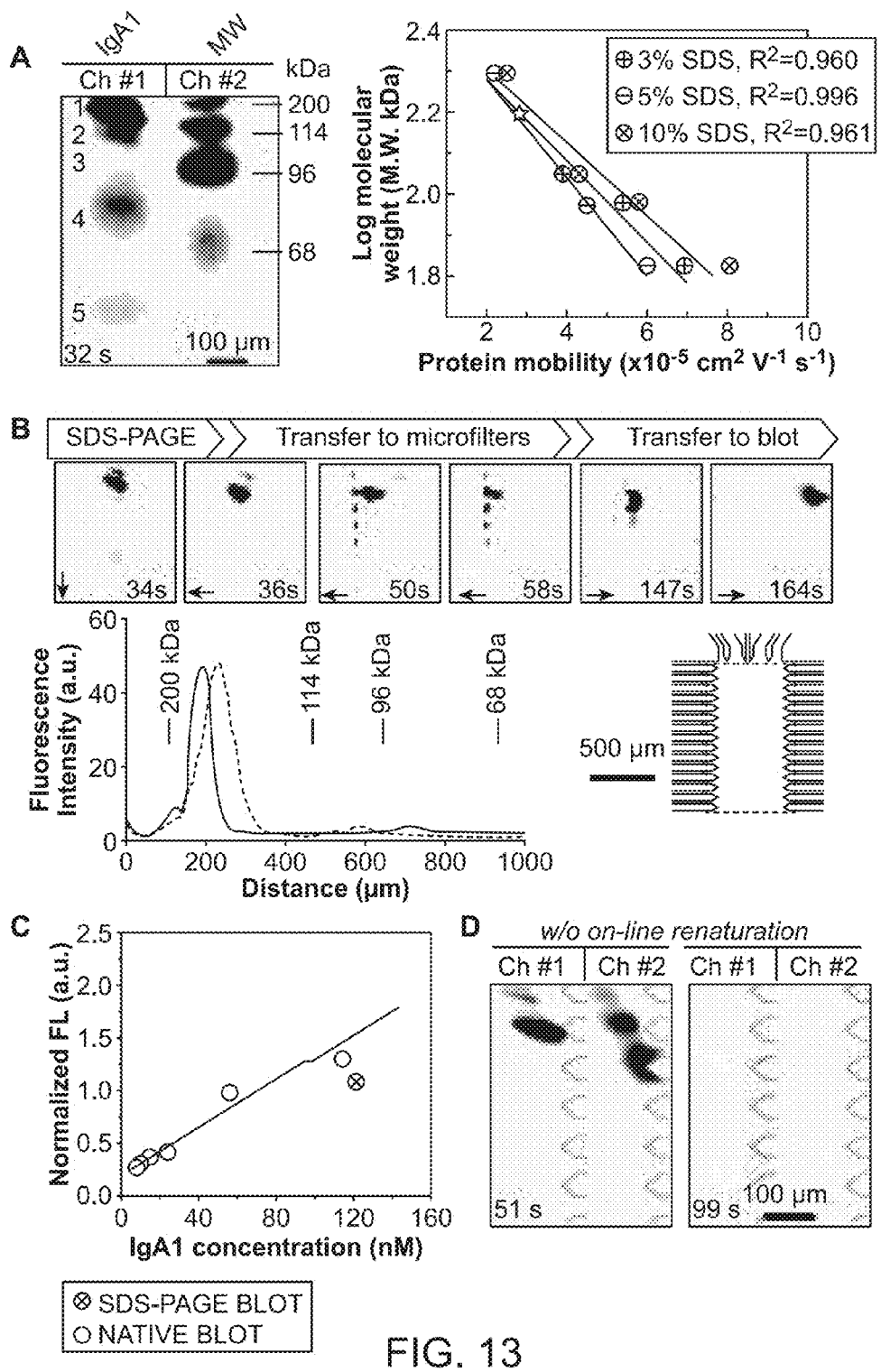
FIG. 13 shows fluorescence micrographs and graphs of a microfluidic HAA lectin blot of galactose-deficient IgA1 myeloma protein, according to embodiments of the present disclosure.

On-chip non-reducing SDS-PAGE of fluorescently labeled galactose-deficient IgA1 myeloma protein (green) was conducted and yielded an average separation resolution (SR) of 1.3 (FIG. 13A) for the five species present. The on-chip analysis was consistent with the slab gel (see FIG. 24(b)), yet required 32 s of separation time. An SDS-PAGE protein ladder (68-200 kDa, labeled with a red fluorophore) was separated simultaneously and observed in a second optical channel (FIG. 13A). FIG. 13(A) shows fluorescence micrographs of two-color monitoring of Mr ladders and myeloma IgA1 sizing. The linear calibration curves (FIG. 13A, right) were obtained using myosin heavy chain (200 kDa), β-galactosidase (114 kDa), phosphorylase B (96 kDa), and human serum albumin (68 kDa) in three SDS treatment conditions (3, 5, and 10% SDS). The linear calibration curves were used for the calculation of unknown protein molecular masses. Two-color monitoring enabled molecular mass (Mr) calibration for unknown proteins and provided size information via a linear calibration curve ($R^2>0.96$). The 5% SDS treatment was applied for sizing of the galactose-deficient IgA1 myeloma protein. Using the calibration relation ($\log(Mr)=(-0.13\times$mobility$)+2.6$), the Mr of IgA1 was determined to be 160 kDa (FIG. 13A), consistent with the expected Mr of monomeric IgA1 (see FIG. 13A, right; the star indicates the size of monomeric IgA1). The sizes of species 3 and 4 were assigned as 141 and 85 kDa, respectively, and were consistent with fragments of IgA; species 3 was consistent with the 141 kDa monomer lacking one light chain (L), and the 85 kDa species 4 was consistent with H (heavy chain)1+L1. Species 3 and 4 were also observed with slab-gel sizing (FIG. 24(b)). Species 5 was free dye (<1 kDa). After non-reducing SDS-PAGE, the species were laterally transferred into the flanking MrCO microfilters for SDS removal and buffer exchange by applying a transfer potential for 100 s, as described previously. Treated protein species were then electrophoresed across the chamber and into the blotting region (FIG. 13B). FIG. 13(B) shows fluorescence micrographs of the time evolution of the HAA lectin blot of galactose-deficient IgA1 myeloma protein. FIG. 13B, bottom, shows a graph of the fluorescence intensity distribution on the separation axis (gray line) compared with the intensity distribution in the blotting array (dashed black line at 164 s). Arrows indicate the direction of electrophoresis. The array channel spacing was ~50 μm. The imaging region is shown in the inset. The loss of Mr information from the SDS-PAGE axis to the final blot axis was ~7 kDa, with SR losses of <5%.

The role of on-chip renaturation and SDS removal to restore lectin recognition of sized proteins was estimated by comparing on-chip lectin blotting of native IgA1 (no SDS present) to blotting of SDS-treated and subsequently renatured IgA1 (FIG. 13C). The fluorescence signal of protein retained in the HAA blotting region indicated about 75% recovery of the lectin-binding capacity for SDS-treated proteins using the MrCO microfilter approach (FIG. 13C). This binding capacity performance was sufficient for assays of serum IgA1, which was the dominant subclass of total serum IgA (>2 mg/mL).

To assess the role of SDS dilution in restoring the lectin binding affinity, lectin blotting of SDS-treated IgA1 without on-chip renaturation and SDS dilution was performed (FIG. 13D). 5% SDS-myeloma IgA1 was directly transferred to the blotting region after on-chip SDS-PAGE, with no treatment at the MrCO microfilters. No detectable binding was observed. Similarly, transfer of a Mr ladder (68-200 kDa) to the HAA blotting region showed no appreciable binding, suggesting negligible non-specific adsorption and size-exclusion effects (FIG. 13D). The microfluidic HAA lectin blot allowed a rapid (~6 min) assessment of IgA1 O-linked galactose deficiency that mimicked serum IgA1 from patients with IgAN.

The above experiments demonstrated a rapid and automated assay that integrated SDS-PAGE, in situ renaturation and SDS-dilution, electrophoretic transfer between stages, and subsequent affinity blotting in a single microfluidic device. An array of MrCO microfilters removed SDS between the sizing and blotting steps and restored the binding affinity for proteins after SDS sizing. Subsequent antibody probing of lectin-captured glycosylated proteins (labeled or unlabeled) resulted in a lectin-glycoprotein-antibody sandwich that was detected to determine the protein size, glycosylation status, and immunoreactivity. While the targeted proteomic assay described in the experiments above has been used for the analysis of IgA1, the assay operational parameters (e.g., separation field strength, buffer constituents) and the device parameters (e.g., separation length, separation-gel pore size distribution, geometry and length scales of flanking arrays) may be adjusted to perform assays of other analytes of interest. Analysis of purified and fluorescently labeled targets was used to determine performance characteristics of the assay (e.g., total assay losses and the on-chip renaturation process).

Slab PAGE Lectin Blotting and *Helix aspersa* (HAA) Affinity

Slab gel SDS PAGE and lectin blotting were performed by using Tris-glycine pH 8.3, 4-12% precast polyacrylamide slab mini-gels with XCell SureLock Mini-Cell & XCell II Blot Module (Invitrogen Novex). For non-reduced SDS-PAGE, proteins were added to 15 μL sample buffer containing 125 mM Tris, pH 8.3, 0.005% bromophenol blue, 20% glycerol, 12% SDS (gel loading volume ~25 μL). Relative molecular masses were estimated using protein standard ladders (All blue, BioRad). Slab PAGE was visualized by post-staining with a Colloidal Blue Staining Kit (Invitrogen). After electrophoresis at 125 V for 2.5 h, gels were electrotransferred to PVDF membranes (0.2 μm) at 25 V for 2.5 h. After washing twice with wash buffer (1×PBS, 0.5% Tween 20, pH 7.4), the PVDF membranes were blocked with phosphate-buffered saline (PBS) containing 1% Tween 20 overnight at 4° C. with shaking. A solution of biotinylated HAA lectin (1 μg/mL) was added into blocking buffer and incubated of 2-h with shaking at room temperature. After incubation, the membrane was washed 3 times for 10 min each. Extravidin-HRP (Invitrogen, ELISA grade, 1.1 mg/mL) diluted 1:2000 in the blocking solution was added and incubated for 1-h at room temperature with agitation. Subsequently, the washing step was repeated three times, followed by rinsing the membrane with water for 1 min. The membrane was subsequently developed with Novex Chromogenic Substrate Reagent (Invitrogen) until the desired band intensity was achieved. Imaging was performed by using ChemiDoc XRS (BioRad) with a proprietary filter.

To correlate the lectin reactivity of a serum sample to its IgA1 molecular identity, Western blotting with anti-IgA antibody (α chain-specific) was performed following the protocol above. Biotin-conjugated goat (Fab')$_2$ anti-human IgA (α-chain-specific, Biosource) was used as the primary antibody to identify the IgA band. This validation indicated that the lectin affinity was solely contributed by IgA1 protein. In the antibody probing case, 1% nonfat dry milk blocking solution (Invitrogen) was used for blocking. Extravidin-HRP (Invitrogen, ELISA grade, 1.1 mg/mL) was used as a secondary antibody by adding it to blocking solution and incubating for 1-h at room temperature. The membrane was subsequently developed with Novex Chromogenic Substrate Reagent (Invitrogen) and Imaged by ChemiDoc XRS (BioRad).

For comparison to on-chip lectin binding efficiency in cross-linked PA blotting gel, the dissociation constant was measured by using a 96-well plate with an active amine surface functionality (round plate, Corning). Following the standard direct ELISA protocols, the biotin-conjugated HAA was immobilized onto well surfaces. The PBS buffer and Super-Block T20 (PBS) Blocking Buffer (Thermo Scientific) were used for the washing and blocking steps. Serial diluted IgA1

(galactose-deficient) solutions in 488 Alexa Fluor labeling were incubated in the wells for 2 h at room temperature. The emission fluorescence was read by using a TECAN plate reader (Infinite V200 Pro).

For on-chip dissociation constant measurements, the blotting gel was fabricated by exposing a region filled with a 5% T, 3.3% C precursor solution (diluted by 1× Tris-glycine native electrophoresis buffer containing 0.4 mg/mL streptavidin-acrylamide and 1 mg/mL biotinylated HAA) to UV excitation (~12.5 mW/cm$^2$) for 330 s. Serial diluted IgA1 (galactose-deficient) solutions with 488 Alexa Fluor labeling were electrophoresed into the microfluidic chip and bound to a blotting gel plug. The bound fluorescence on the blotting gel was measured. The dissociation constant was obtained by fitting the response curves in the following binding equation:

$$B=B_{max}*C/(K_d+C),$$

where B is the signal from binding complex, and C is the antigen concentration. Compared to FIG. 24, which shows slab gel SDS PAGE and lectin blotting, the microfluidic chip porous polymer networks produced a heterogeneous phase and yielded a high surface-area to volume ratio structure, which allowed for more efficient binding. In conjunction with the lectin-bound polymeric materials, electrophoretic transport was used to transfer proteins in the sample in proximity to the HAA binding sites, thus facilitating the binding process.

Although the foregoing embodiments have been described in some detail by way of illustration and example for purposes of clarity of understanding, it is readily apparent to those of ordinary skill in the art in light of the teachings of the present disclosure that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A microfluidic device comprising:
a separation medium having a first flow path with a first flow direction;
a protein renaturation component in fluid communication with the separation medium and having a second flow path with a second flow direction; and
a binding medium in fluid communication with the separation medium and having a third flow path with a flow direction different from the second flow direction.

2. The microfluidic device according to claim 1, wherein the first flow path has a first directional axis and the second flow path has a second directional axis.

3. The microfluidic device according to claim 1, wherein the second flow path and the third flow path are in opposite directions along the second directional axis.

4. The microfluidic device according to claim 1, wherein the protein renaturation component comprises a sub-nanopore gel membrane.

5. The microfluidic device according to claim 4, wherein the sub-nanopore gel membrane is polymerized from a precursor having a monomer concentration ranging from 40 to 50% T.

6. The microfluidic device according to claim 1, wherein the binding medium comprises a binding member stably associated with a support.

7. The microfluidic device according to claim 6, wherein the binding member is a proteinaceous binding member.

8. The microfluidic device according to claim 7, wherein the proteinaceous binding member comprises an antibody or a binding fragment thereof.

9. The microfluidic device according to claim 8, wherein the proteinaceous binding member comprises a lectin.

10. The microfluidic device according to claim 1, wherein the device further comprises a loading medium in fluid communication with the separation medium.

11. The microfluidic device according to claim 10, wherein the device is configured so that the renaturation component bounds a first side of the separation medium, a binding medium bounds a second side of the separation medium that is opposite the first side, and the loading medium bounds a third side of the separation medium that is between the first and second sides.

12. The microfluidic device according to claim 11, further comprising a first set of side channels comprising the renaturation component, and a second set of side channels comprising the binding medium.

13. The microfluidic device according to claim 11, wherein the device is configured to apply first and second electric fields of differing directions to the separation medium.

14. The microfluidic device according to claim 13, wherein the first and second electric fields are orthogonal to each other.

15. The microfluidic device according to claim 1, further comprising a buffer.

16. The microfluidic device according to claim 15, wherein the buffer comprises a detergent.

17. The microfluidic device according to claim 15, further comprising a sample.

18. The microfluidic device according to claim 17, wherein the sample comprises an analyte of interest.

19. The microfluidic device according to claim 18, wherein the analyte comprises a fluorescent label.

20. The microfluidic device according to claim 1, wherein the separation medium is in direct contact with the protein renaturation component.

21. The microfluidic device according to claim 1, wherein the separation medium is in direct contact with the binding medium.

22. A kit comprising
(a) a microfluidic device comprising:
  (i) a separation medium having a first flow path with a first flow direction;
  (ii) a protein renaturation component in fluid communication with the separation medium and having a second flow path with a second flow direction;
  (iii) a binding medium in fluid communication with the separation medium and having a third flow path with a flow direction different from the second flow direction; and
(b) a labeled binding member.

23. The kit according to claim 22, further comprising one or more reagents selected from the group consisting of a buffer, a detection reagent, a release reagent, a detergent, a refolding reagent and a denaturing reagent.

* * * * *